(12) United States Patent
Osborne

(10) Patent No.: US 12,390,453 B2
(45) Date of Patent: *Aug. 19, 2025

(54) METHOD FOR REDUCING SIDE EFFECTS FROM ADMINISTRATION OF PHOSPHODIESTERASE-4 INHIBITORS

(71) Applicant: ARCUTIS BIOTHERAPEUTICS, INC., Westlake Village, CA (US)

(72) Inventor: David W. Osborne, Fort Collins, CO (US)

(73) Assignee: ARCUTIS BIOTHERAPEUTICS, INC., Westlake Village, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/670,960

(22) Filed: May 22, 2024

(65) Prior Publication Data

US 2024/0374576 A1    Nov. 14, 2024

Related U.S. Application Data

(63) Continuation of application No. 18/353,870, filed on Jul. 17, 2023, now Pat. No. 12,042,487, which is a continuation of application No. 17/327,236, filed on May 21, 2021, now Pat. No. 11,992,480, which is a continuation of application No. 16/563,435, filed on Sep. 6, 2019, now abandoned.

(60) Provisional application No. 62/768,314, filed on Nov. 16, 2018.

(51) Int. Cl.
| | |
|---|---|
| *A61K 31/44* | (2006.01) |
| *A61K 9/00* | (2006.01) |
| *A61K 9/06* | (2006.01) |
| *A61K 9/12* | (2006.01) |
| *A61K 45/06* | (2006.01) |
| *A61K 47/10* | (2017.01) |
| *A61K 47/24* | (2006.01) |
| *A61P 19/02* | (2006.01) |

(52) U.S. Cl.
CPC ............ *A61K 31/44* (2013.01); *A61K 9/0014* (2013.01); *A61K 9/06* (2013.01); *A61K 9/122* (2013.01); *A61K 47/10* (2013.01); *A61K 47/24* (2013.01); *A61P 19/02* (2018.01); *A61K 45/06* (2013.01)

(58) Field of Classification Search
CPC ........ A61K 31/44; A61K 9/0014; A61K 9/06; A61K 47/10; A61K 47/24; A61K 9/122; A61K 45/06; A61P 19/02
See application file for complete search history.

(56) References Cited

U.S. PATENT DOCUMENTS

| | | |
|---|---|---|
| 4,482,537 A | 11/1984 | El-Menshawy et al. |
| 5,374,661 A | 12/1994 | Betlach, II |
| 5,712,298 A | 1/1998 | Amschler |
| 5,863,560 A | 1/1999 | Osborne |
| 6,056,955 A | 5/2000 | Fischetti et al. |
| 6,060,085 A | 5/2000 | Osborne |
| 6,106,848 A | 8/2000 | Preuilh et al. |
| 6,117,915 A | 9/2000 | Pereira et al. |
| 6,214,322 B1 | 4/2001 | Castro et al. |
| 7,470,791 B2 | 12/2008 | Kohl et al. |
| 7,951,398 B2 | 5/2011 | Dietrich et al. |
| 8,293,288 B2 | 10/2012 | Ma |
| 8,338,648 B2 | 12/2012 | Stock et al. |
| 8,536,206 B2 | 9/2013 | Kohl et al. |
| 8,618,142 B2 | 12/2013 | Kohl et al. |
| 9,205,044 B2 | 12/2015 | Linder |
| 9,649,302 B2 | 5/2017 | Vakkalanka |
| 9,884,050 B1 | 2/2018 | Osborne |
| 9,895,359 B1 | 2/2018 | Osborne |
| 9,907,788 B1 | 3/2018 | Osborne |
| 10,092,588 B2 | 10/2018 | Tamarkin |
| 10,105,354 B1 | 10/2018 | Osborne |
| 10,172,841 B2 | 1/2019 | Osborne |
| 10,940,142 B2 | 3/2021 | Osborne |
| 10,987,290 B2 | 4/2021 | Wei |
| 11,129,818 B2 | 9/2021 | Osborne et al. |
| 11,534,493 B2 | 12/2022 | Osborne |
| 11,707,454 B2 | 7/2023 | Berk |
| 11,793,796 B2 | 10/2023 | Osborne |
| 11,819,496 B2 | 11/2023 | Osborne |
| 2005/0112162 A1 | 5/2005 | Drader |
| 2005/0244339 A1 | 11/2005 | Jauernig et al. |
| 2006/0084684 A1 | 4/2006 | Bolle |
| 2006/0153905 A1 | 7/2006 | Carrara |

(Continued)

FOREIGN PATENT DOCUMENTS

| | | |
|---|---|---|
| CN | 1655782 | 8/2005 |
| EP | 1511516 | 3/2005 |
| JP | 2005529930 A | 10/2005 |
| JP | 2007533606 A | 11/2007 |
| JP | 2011219364 A | 11/2011 |

(Continued)

OTHER PUBLICATIONS

Notification of Certification of Invalidity, Unenforceability, and/or Non-Infringement for U.S. Pat. No. 12,042,487 Pursuant to § 505(j)(2)(B)(iv) of the Federal Food, Drug, and Cosmetic Act, Sep. 12, 2024, 107 pages.

(Continued)

*Primary Examiner* — Shirley V Gembeh
(74) *Attorney, Agent, or Firm* — Rothwell, Figg, Ernst & Manbeck, P.C.

(57) ABSTRACT

A method for altering the PK profile of a pharmaceutical formulation containing a PDE-4 inhibitor, such as roflumilast, to reduce the spike in Cmax. The spike in Cmax is reduced by topically administering the PDE-4 inhibitor in combination with one or more phosphate ester surfactants. Reducing the spike in Cmax will reduce gastrointestinal side effects and result in better patient compliance.

23 Claims, 11 Drawing Sheets

(56) References Cited

U.S. PATENT DOCUMENTS

| | | | |
|---|---|---|---|
| 2006/0204452 A1 | 9/2006 | Lathrop et al. | |
| 2006/0204526 A1 | 9/2006 | Lathrop | |
| 2006/0234006 A1 | 10/2006 | Terra | |
| 2007/0048241 A1 | 3/2007 | Obukowho et al. | |
| 2007/0207107 A1 | 9/2007 | Winckle et al. | |
| 2007/0259009 A1 | 11/2007 | Linder | |
| 2007/0287689 A1 | 12/2007 | Harada | |
| 2008/0039405 A1 | 2/2008 | Langley | |
| 2008/0045572 A1 | 2/2008 | Linder | |
| 2008/0280958 A1 | 11/2008 | Bolle et al. | |
| 2009/0104132 A1 | 4/2009 | Segura-Orsoni | |
| 2009/0111780 A1 | 4/2009 | Giordano | |
| 2009/0214628 A1 | 8/2009 | De Rijk | |
| 2009/0215836 A1 | 8/2009 | Beume | |
| 2009/0220583 A1 | 9/2009 | Pereswetoff-Morath et al. | |
| 2011/0117182 A1 | 5/2011 | Ahluwalia et al. | |
| 2011/0212157 A1 | 9/2011 | Edelson et al. | |
| 2012/0252793 A1 | 10/2012 | Bream et al. | |
| 2013/0005816 A1 | 1/2013 | Chen | |
| 2013/0017282 A1 | 1/2013 | Ma | |
| 2013/0018104 A1 | 1/2013 | Lathrop et al. | |
| 2013/0217742 A1 | 8/2013 | Yang | |
| 2014/0112991 A1 | 4/2014 | Johnson et al. | |
| 2014/0275184 A1 | 9/2014 | Jones et al. | |
| 2014/0275265 A1 | 9/2014 | Mattison | |
| 2014/0296191 A1 | 10/2014 | Patel et al. | |
| 2014/0303215 A1 | 10/2014 | Bolle et al. | |
| 2015/0099752 A9 | 4/2015 | Bernal Anchuela et al. | |
| 2015/0297601 A1 | 10/2015 | Henkin | |
| 2016/0030435 A1 | 2/2016 | Henkin | |
| 2017/0152273 A1 | 6/2017 | Merchant | |
| 2017/0266289 A1 | 9/2017 | Kipari | |
| 2018/0353490 A1 | 12/2018 | Osborne | |
| 2019/0091333 A1 | 3/2019 | Osborne | |
| 2019/0175491 A1 | 6/2019 | Abraham et al. | |
| 2019/0365642 A1 | 12/2019 | Osborne | |
| 2020/0155524 A1 | 5/2020 | Welgus et al. | |
| 2021/0161870 A1 | 6/2021 | Welgus et al. | |
| 2021/0275509 A1 | 9/2021 | Welgus et al. | |
| 2021/0386719 A1 | 12/2021 | Osborne et al. | |
| 2022/0211730 A1 | 7/2022 | Osborne et al. | |
| 2023/0091358 A1 | 3/2023 | Osborne et al. | |
| 2023/0201177 A1 | 6/2023 | Osborne | |
| 2023/0285319 A1 | 9/2023 | Osborne et al. | |
| 2023/0310345 A1 | 10/2023 | Osborne et al. | |

FOREIGN PATENT DOCUMENTS

| | | |
|---|---|---|
| WO | 9501338 | 1/1995 |
| WO | 9810768 | 3/1998 |
| WO | 2003099334 | 12/2003 |
| WO | WO 2005/016296 A1 | 2/2005 |
| WO | 2005115322 | 12/2005 |
| WO | 2006073559 A1 | 7/2006 |
| WO | 2008009616 A2 | 1/2008 |
| WO | 2009069006 A2 | 6/2009 |
| WO | 2013030789 | 3/2013 |
| WO | 2013081565 | 6/2013 |
| WO | 2014055801 | 4/2014 |
| WO | 2014130922 | 8/2014 |
| WO | 2014201541 | 12/2014 |
| WO | 2015132708 | 9/2015 |
| WO | 2016033308 | 3/2016 |
| WO | 2017216738 | 12/2017 |
| WO | 2018226584 | 12/2018 |
| WO | 2019060379 | 3/2019 |
| WO | 2021045804 | 3/2021 |

OTHER PUBLICATIONS

Communication of a Notice of Opposition Against European Patent No. 3 634 380, Sep. 26, 2024, 22 pages.
Felton "Remington: Essentials of Pharmaceutics" London: Pharmaceutical Press (2012), 54 pages.
"Hexylene Glycol GPS Safety Summary," Arkema, Apr. 30, 2012, 5 pages.
Article 94(3) communication in EP 20861685.4 issued Oct. 8, 2024, 5 pages.
Notification of Certification of Invalidity, Unenforceability, and/or Non-Infringement for U.S. Pat. Nos. 11,992,480; 12,005,051; 12,005,052; 12,011,437; and 12,016,848 Pursuant to § 505(j)(2)(B)(iv) of the Federal Food, Drug, and Cosmetic Act, Jul. 16, 2024, 290 pages.
Bethke et al. (2007) "Dose-Proportional Intraindividual Single and Repeated-Dose Pharmacokinetics of Roflumilast, an Oral, Once-Daily Phosphodiesterase 4 Inhibitor" *Journal of Clinical Pharmacology* 47:26-36.
Heo et al. (2010) "Topical effects of roflumilast on 1-chloro-2,4-dinitrobenzene-induced atopic dermatitis-like skin lesions in NC/Nga mice" *Pharmazie* 65:906-12.
Jin et al. (2012) "Phosphodiesterase 4 and Its Inhibitors in Inflammatory Diseases" *Chang Gung Medical Journal* 35(3):197-210.
Pleasants (2018) "Clinical Pharmacology of Oral Maintenance Therapies for Obstructive Lung Diseases" *Respiratory Care* 63(6):671-89.
Rabe (2011) "Update on roflumilast, a phosphodiesterase 4 inhibitor for the treatment of chronic obstructive pulmonary disease" *British Journal of Pharmacology* 163:53-67.
Communication of a Notice of Opposition Against European Patent No. 3 684 334, Aug. 20, 2024, 26 pages.
Gattefosse (2015) "Efficient Skin Delivery: No. Compromise With Transcutol®" https://api.semanticscholar.org/CorpusID:203610770, 17 pages.
Fenton (2012) "Handbook of Pharmaceutical Excipients" *Pharmaceutical Press* (7th Ed.), 5 pages.
Osborne (2008) "Review of Changes in Topical Drug Product Classification" *Pharmaceutical Technology* 32:10, 8 pages.
Aulton (2013) "Aulton's Pharmaceutics" *Elsevier Ltd* (4th Ed.), 20 pages.
Office Action issued Jun. 26, 2024 in CN 202080075942.X, 15 pages.
Akhtar et al., "Exploring preclinical and clinical effectiveness of nanoformulations in the treatment of atopic dermatitis: Safety aspects and patent reviews," Bulletin of Faculty of Pharmacy, Cairo University 55 (2017), 1-10.
Bardin P et al. "Roflumilast for asthma: Efficacy findings in mechanism of action studies." Pulmonary Pharmacology & Therapeutics, vol. 35, Aug. 19, 2015, S4-S10.
Brown, "Treating COPD with PDE 4 inhibitors", International Journal of COPD 2007: 2(4) 517-533.
Examination Report cited in India Application No. 20194705011 dated Jul. 9, 2021. 6 pages.
Examination Report cited in India Application No. 202047016247 dated Jun. 28, 2021. 4 pages.
Final Office Action issued in U.S. Appl. No. 15/712,900 dated May 23, 2022. 14 pages.
Huang, J. et al., "Pharmacokinetics of single- and multiple-dose roflumilast: an open-label, three-way crossover study in healthy Chinese volunteers." Drug Design, Development and Therapy, 2018(12). pp. 4047-4057.
International Search Report and Written Opinion cited in PCT/US2018/051691 dated Nov. 22, 2018, 11 pages.
International Preliminary Report on Patentability and Written Opinion cited PCT/US2018/051691 dated Mar. 24, 2020. 6 pages.
International Preliminary Report on Patentability and Written Opinion cited I PCT/US2018/051691 dated Apr. 2, 2020. 8 pages.
International Search Report issued in PCT/US2021/031144 dated Sep. 21, 2021. 12 pages.
Ip.com translation KR1999-0015251 A, printed 2022 (year2022), 1 page.
Julian N. Mayba et al. Review of Atopic Dermatitis and Topical Therapies:, Journal of Cutaneous Medicine and Surgery, BC Decker Inc. CA. vol. 21 No. 3 Dec. 27, 2016, pp. 227-236.
Karande et al., "Enhancement of transdermal drug delivery via synergistic action of chemicals", Biochimica Et Biophysica Acta, 1788 (2009), pp. 2632-2373.

(56) References Cited

OTHER PUBLICATIONS

Kawamatawong, "Roles of roflumilast, a selective phosphodiesterase 4 inhibitor in airway diseases," J. Thorac Dis 2017. 9(4). 1144-1154.
Kircik, L et al., "Rational Vehicle Design Ensures Targeted Cutaneous Steroid Delivery." Journal of Clinical and Aesthetic Dermatology 10(2). Feb. 2017. pp. 12-19.
Lorimer, "Thermodynamics of solubility in mixed solvent systems", Pure & Appl. Chem., 1993, vol. 65, 2, pp. 183-191.
Minghetti et al., "Ex Vivo Study of Transdermal Permeation of Four Diclofenac Salts from Different Vehicles", Journal of Pharmaceutical Sciences, vo. 96, No. 4, Apr. 2007, pp. 814-823.
Nair et al., "Basic considerations in the dermatokinetics of topical formulations", Brazilian Journal of Pharmaceutical Sciences, vol. 43, No. 3, Jul./Sep. 2013, pp. 423-434.
Notification of Transmittal of the International Search Report and The Written Opinion of the International Searching Authority cited in PCT/US2020/29008 dated Jul. 6, 2020. 13 pages.
Notification of Transmittal of the International Search Report and Written Opinion cited in PCT/US2019/034640 dated Dec. 4, 2019, 10 pages.
Notification of Transmittal of the International Search Report and The Written Opinion of the International Searching Authority cited in PCT/US2021/015740 dated Apr. 23, 2021. 17 pages.
Notification of Transmittal of the International Search Report and Written Opinion of the International Searching Authority issued in PCT/US2022/013344 dated Jun. 9, 2022, 16 pages.
Notification of Transmittal of the International Search Report and the Written Opinion of the International Searching Authority issued in PCT/US2021/061871, dated Apr. 5, 2022. 12 pages.
Notification of Transmittal of the International Search Report and Written Opinion cited in PCT/US2019/034640, dated Dec. 4, 2019, 14 pages.
Office Action issued in MX/a/2019/014741 dated Nov. 4, 2022 (7 pages).
Osborne, "Diethylene glycol monoethyl ether: an emerging solvent in topical dermatology products", J. Cosmet Dermatol, Dec. 2011, 10(4), pp. 324-329.
Pathan et al., "Chemical Penetration Enhancers for Transdermal Drug Delivery Systems", Tropical Journal of Pharmaceutical Research, Apr. 2009, 8(2), pp. 173-179.
Patzelt et al., "Hair follicles, their disorders and their opportunities", Drug Discovery Today: Disease Mechanisms, vol. 5, Issue 2, Summer 2008, pp. e173-e-181.
PCT International Search Report and Written Opinion issued in PCT/US2018/0358584 on Aug. 17, 2018, 12 pages.
Pudipeddi et al., "Trends in Solubility of Polymorphs", Journal of Pharmaceutical Sciences, May 2005, vol. 94, Issue 5, pp. 929-939, Abstract only.
Shakeel et al. "Solubilization behavior of paracetamol in Transcutol—water mixtures at (298.15 to 333.15) K," Journal of Chemical & Engineering Data 58:3551-3556, 2013.
Sikarra et al., "Techniques for Solubility Enhancement of Poorly Soluble Drugs: An Overview", Journal of Medical Pharmaceutical and Allied Sciences, (2012), 01; pp. 1-22.
Snape et al., "A phase I randomized trial to assess the effect on skin infiltrate thickness and tolerability of topical phosphodiesterase inhibitors in the treatment of psoriasis vulgaris using a modified psoriasis plaque test", British Journal of Dermatology (2016) 175, pp. 479-486.
Special Chem "Ethoxydiglycol ," printed 2019; https://cosmetics.specialchem.com/inci/ethoxydiglycol.
Tradename (roflumilast) Tablets NDA 22-522, Summary of Basis for the Recommended Action from Chemistry, Manufacturing, and Controls, Forest Research Institute, Inc., Reference ID 2901509, Jul. 2009, 3 pages.
Translation Abstract. of Office Action for Chinese Patent Application No. 201810581282.7 dated Oct. 22, 2019; 13 pages.
Wikipedia "Corticosteroid," last edited Nov. 15, 2019; https://en.wikipedia.org/wiki/Corticosteroid.

Wittmann et al. "Phosphodiesterase 4 Inhibition in the Treatment of Psoriasis, Psoratic Arthritis and Other Chronic Inflammatory Diseases". Dermatol Ther(Heidelb) (2013) 3:1-15.
E P Bezuglaya et al., "Water-Hexylene Glycol System as A Potential Medicinal Base", Pharmaceutical Chemistry, vol. 47, pp. 281-286. 2013.
Pre-grant Opposition documents filed for Indian Application No. 201947050111, Apr. 5, 2023, 38 pages.
T. Gao, et al., "Sunscreen Formulas with Multilayer Lamella Structure," Cosmetics & Toiletries, vol. 118, pp. 41-52 (Oct. 2003).
D.Y.M. Leung, et al., "New Insights into Atopic Dermatitis," J. Clin. Invest., vol. 113, pp. 651-657 (2004).
L. Kircik, "Topical Treatment Adherence for Psoriasis," Skin Therapy Letter—Family Practice Edition, vol. 4, No. 2, pp. 4 & 5 (2008).
S.R. Feldman, et al., "Psoriasis: Improving Adherence to Topical Therapy," J. Am. Acad. Dermatol., vol. 59, pp. 1009-1016 (2008).
S.M. Ali, et al., "Skin pH: From Basic Science to Basic Skin Care," Acta Derm. Venereal., vol. 93, pp. 261-267 (1-9), Tbl. SI (2013).
Study NCT01856764, "Topical Roflumilast in Adults with Atopic Dermatitis," sponsored by Takeda, available at https://clinicaltrials.gov/ (Jul. 2015).
Y. Javadzadeh, et al., "Transcutol® (Diethylene Glycol Monoethyl Ether): A Potential Penetration Enhancer," Ch. 12, pp. 195-205, in N. Dragicevic, et al., eds., Percutaneous Penetration Enhancers Chemical Methods in Penetration Enhancement: Modification of the Stratum Corneum (2015).
D.W. Osborne, et al., "Skin Penetration and Permeation Properties of Transcutol®—Neat or Diluted Mixtures," AAPS PharmSciTech, vol. 19, pp. 3512-3533 (2018).
FDA, Inactive Ingredient Guide (Jan. 1996).
M.J. O'Neil, et al., eds., The Merck Index, pp. 2822, 8379 (15th ed., 2013).
Labeling for Elocon® (mometasone furoate) Cream (2013).
Labeling for Daliresp® (roflumilast) Tablets (2013).
Physicians' Desk Reference, pp. 305, 748-52, 1432-35 (67th/2013 ed., 2012).
I.M. Rosenstock, "Understanding and Enhancing Patient Compliance with Diabetic Regimens," Diabetes Care, vol. 8, pp. 610-616 (1985).
J. Urquhart, "The Electronic Medication Event Monitor: Lessons for Pharmacotherapy," Clin. Pharmacokinet., vol. 32, pp. 345-356 (1997).
S.S. Zaghloul, et al., "Objective Assessment of Compliance with Psoriasis Treatment," Arch. Dermatol., vol. 140, pp. 408-414 (2004).
P. Assawasuwannakit, et al., "Quantification of the Forgiveness of Drugs to Imperfect Adherence," CPT Pharmacometrics Syst. Pharmacol., vol. 4, e4, pp. 1-8 (2015).
Office Action issued in U.S. Appl. No. 18/453,674 dated Oct. 27, 2023 (13 pages).
Office Action issued in U.S. Appl. No. 17/155,679 dated Feb. 5, 2024 (9 pages).
Office Action issued in U.S. Appl. No. 18/345,692 dated Oct. 26, 2023 (68 pages).
Office Action issued in U.S. Appl. No. 18/345,732 dated Jan. 24, 2024 (12 pages).
Office Action issued in U.S. Appl. No. 18/345,760 dated Oct. 26, 2023 (19 pages).
Office Action issued in U.S. Appl. No. 18/353,870 dated Jan. 12, 2024 (10 pages).
Office Action issued in U.S. Appl. No. 18/353,869 dated Sep. 18, 2023 (7 pages).
Notification of Certification of Invalidity, Unenforceability, and/or Noninfringement for U.S. Pat. Nos. 9,884,050; 9,907,788; 10,940,142; 11,129,818; 11,793,796; and 11,819,496 Pursuant to § 505(j)(2)(B)(iv) of the Federal Food, Drug, & Cosmetic Act, Feb. 13, 2024.
Office Action issued for U.S. Appl. No. 17/821,051 on Jan. 29, 2025, 13 pages.
Office Action issued for U.S. Appl. No. 18/345,760 on Dec. 19, 2024, 43 pages.
Office Action issued for U.S. Appl. No. 17/887,798 on Dec. 19, 2024, 91 pages.
Non-Final Office Action issued for U.S. Appl. No. 18/345,760 on May 8, 2025, 23 pages.

A. Change from baseline in TPSS×TPA (primary efficacy endpoint)

B. Change from baseline in TPSS (secondary efficacy endpoint)

C. Change from baseline in TPA (secondary efficacy endpoint)

METHOD FOR REDUCING SIDE EFFECTS FROM ADMINISTRATION OF PHOSPHODIESTERASE-4 INHIBITORS

CROSS REFERENCE OF RELATED APPLICATION

This application a continuation of U.S. application Ser. No. 18/353,870, filed on Jul. 17, 2023, which is a continuation of U.S. application Ser. No. 17/327,236, filed on May 21, 2021, now patented, which is a continuation of Ser. No. 16/563,435, filed Sep. 6, 2019, now abandoned, which claims the benefit under 35 U.S.C. § 119(e) of the filing date of provisional patent application Ser. No. 62/768,314 filed Nov. 16, 2018, the disclosures of which are incorporated herein by reference in their entirety.

FIELD OF THE INVENTION

The present invention pertains to the field of topical medications for the treatment of medical disorders. In particular, the invention pertains to topical formulations containing an active pharmaceutical ingredient that is an inhibitor of the enzyme phosphodiesterase-4. The formulations are pharmaceutically efficacious but have decreased gastrointestinal side effects.

BACKGROUND OF THE INVENTION

Drugs that inhibit the enzyme phosphodiesterase-4 (PDE-4) have been found to be useful in the medical treatment of many medical conditions, most notably psoriatic arthritis, psoriasis, atopic dermatitis, asthma, and chronic obstructive pulmonary disease (COPD). Examples of such drugs include apremilast, cilomilast, crisaborole, ibudilast, piclamilast, roflumilast, and rolipram. Although these drugs are clinically useful, their use has been limited at times due to the high incidence of side effects including diarrhea, weight loss, nausea, headache, back pain, insomnia, dizziness, flu-like symptoms and decreased appetite, that are associated with their administration. These side effects, especially the gastrointestinal side effects, can have a significant influence on patient compliance.

Roflumilast (3-cyclopropylmethoxy-4-difluoromethoxy-N-[3,5-di-chloropyrid-yl]-benzamide) and its active metabolite roflumilast N-oxide (3-cyclopropylmethoxy-4-difluoromethoxy-N-(3,5-dichloropyrid-4-yl 1-oxide)benzamide) are described herein as representative members of the class of drugs that inhibit PDE-4. Roflumilast is known to be suitable as a bronchial therapeutic agent as well as for the treatment of inflammatory disorders. Compositions containing roflumilast are used in human and veterinary medicine and have been proposed for the treatment and prophylaxis of diseases including but not limited to: inflammatory and allergen-induced airway disorders (e.g. bronchitis, asthma, COPD); dermatoses (e.g. proliferative, inflammatory and allergen induced skin disorders), and generalized inflammations in the gastrointestinal region (Crohn's disease and ulcerative colitis). Currently, roflumilast is administered systemically to treat inflammatory disorders involving the lungs, such as asthma and chronic obstructive pulmonary disease (COPD).

Roflumilast and its synthesis were described in U.S. Pat. No. 5,712,298 (the "298 patent"), incorporated herein by reference. Unless otherwise indicated, references incorporated herein by reference are incorporated in their entireties for all purposes. Roflumilast is approved in the United States under the trade name DALIRESP®(AstraZeneca Pharmaceuticals LP, Wilmington, DE) and in Europe under the trade name DAXAS® (Takeda GmbH, Konstanz, Germany). Both DALIRESP® and DAXAS® are administered orally once daily as 500 mcg tablets for treatment of COPD.

Because of the high incidence of gastrointestinal side effects, including severe nausea and diarrhea, the prescribing information pertaining to DALIRESP® instructs that it may be beneficial to take half of the therapeutically effective dose, 250 mcg, once daily for 4 weeks prior to commencing the therapeutically effective dose of 500 mcg per day in order to reduce the rate of treatment discontinuation. The prescribing information for DAXAS® does not instruct the patient to take a reduced non-therapeutically effective dosage prior to taking the therapeutic dose. However, the prescribing information for DAXAS® does report a high incidence of diarrhea, nausea, and abdominal pain associated with this medication.

When roflumilast is orally administered, the drug is rapidly absorbed, resulting in a sharp spike in plasma concentration. According to documents filed in the FDA, upon initial administration of a roflumilast tablet, a Cmax (peak plasma concentration) of 7.34 mcg/l that spiked at a Tmax (time after administration to reach Cmax) 1 hour after administration occurred with a 500 mcg tablet and a Cmax of 3.99 mcg/l that spiked at a Tmax of 1 hour occurred with a 250 mcg tablet. The spike in Cmax followed a clear dose-response relationship. A similar dose-response relationship was shown for the occurrence of gastrointestinal side effects, indicating that these side effects are associated with the spike in Cmax.

When multiple doses of oral roflumilast are administered, exposure follows a 'peak to trough' pattern. This results in an episodic variation in blood levels of drug and continued gastrointestinal side effects due to the renewed high spike Cmax levels following each administration of the drug.

Bolle, U.S. Patent Application Publication No. 2006/0084684 discloses topical formulations of roflumilast, salts of roflumilast, the N-oxide of roflumilast, and salts of the N-oxide. Bolle discloses that such formulations are useful to apply to skin lesions for the local treatment of skin disorders or to administer topically for the systemic treatment of skin disorders and other disorders, such as COPD. Bolle discloses that the systemic effect of topical application of the roflumilast formulations is comparable to that of an oral dosage form.

Bolle further discloses, in paragraph 0080 that "Comparison with oral administration shows that, irrespective of the composition of the topical preparation, similar Cmax and AUCs and similar excretions with the urine are achieved."

Although Bolle does not discuss the incidence of side effects that occur following topical administration of the roflumilast formulations, because Cmax with the topical formulations, irrespective of the composition of the topical formulation, is similar to that which is obtained with orally administered formulations, and because side effects are correlated with Cmax, it would be expected that administration of any of the topical formulations, irrespective of composition, would cause an incidence of side effects similar to that caused by orally administered formulations.

Although oral tablets of roflumilast have been commercialized, topical and parenteral administration require different formulations due to the low aqueous solubility of the compound which has been reported to be only 0.53 mg/l at 21° C. in WO95/01338 (corresponding to the '298 patent and incorporated herein by reference). This low aqueous solubility has been problematic for the development of parenteral preparations and topical emulsions, suspensions, gels or solutions containing water. In U.S. Pat. No. 9,205,044 (incorporated herein by reference), the poor water solubility of roflumilast was overcome by using an alkoxylated fat, specifically polyoxyethylated 12-hydroxystearic acid, as a co-solvent for parenteral administration. In U.S. Pat. No. 9,884,050 (incorporated herein by reference), the poor water solubility of roflumilast was overcome by using hexylene glycol. In EP 1511516B1 (corresponding to published U.S. application Ser. No. 14/075,035 incorporated herein by reference), the low water solubility of roflumilast was overcome in topical emulsion (cream) formulations by formulating with polyethylene glycol 400 (PEG 400) in concentrations over 62% (w/w) while keeping water weight percentages under 10%.

Topical application of potent pharmacological agents like roflumilast has been found to provide superior delivery and greater ease of use for patients. The molecular structure of the compound ultimately dictates the ability of the drug to cross the epithelium of the tissue to which the product is applied. For topical application to skin, selection of the components of the formulation dictates the maximum skin permeation that the formulator can achieve. Creams, lotions, gels, ointments and foams are just a few of the more familiar forms of topical products that contain active pharmaceutical ingredients (API) for application to the skin.

It would be advantageous to develop and provide a pharmaceutical formulation containing a PDE-4 inhibitor, such as roflumilast, that, when administered systemically, in a therapeutically effective dose, does not result in a spike in Cmax, while still providing a high AUC, and which, therefore, is pharmaceutically efficacious but is associated with a decreased incidence of gastrointestinal side effects.

SUMMARY OF THE INVENTION

In accordance with the present invention, it has been discovered that the inclusion of one or more phosphate ester surfactants in a topical formulation containing a PDE-4 inhibitor reduces the spike in Cmax while still producing a high AUC. The reduction in the spike in Cmax reduces gastrointestinal side effects which will lead to better patient compliance.

DESCRIPTION OF THE INVENTION

Figure 1:
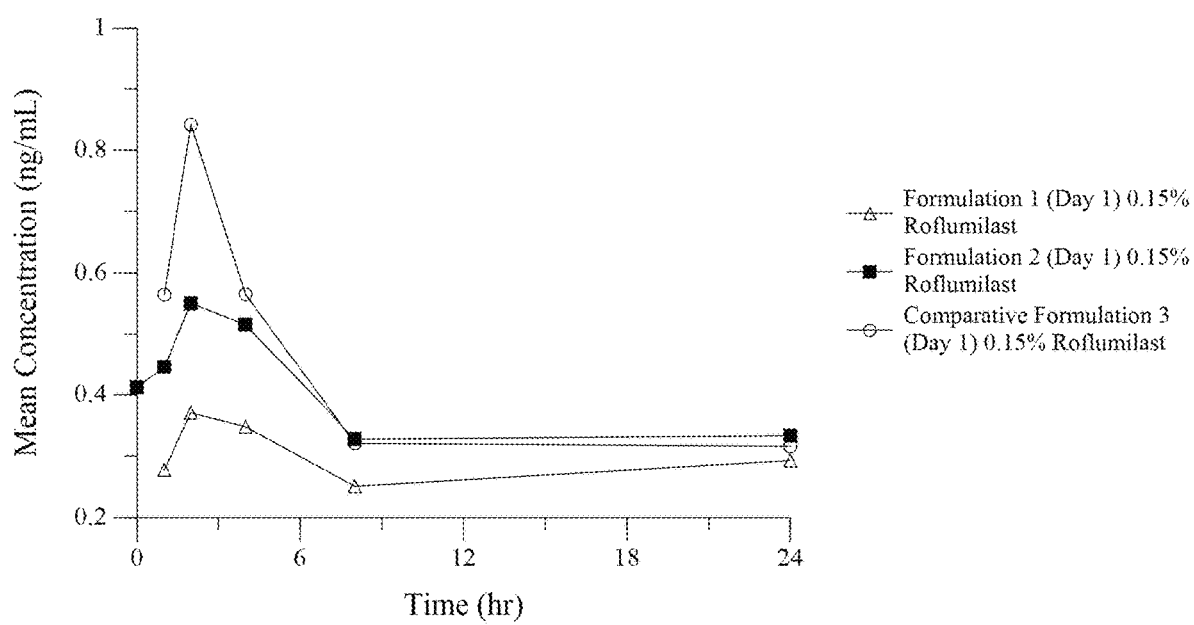
FIG. 1 is a line graph comparing the pharmacokinetic (PK) profile of two formulations of the invention, Formulation 1 and Formulation 2, and a PK profile of a formulation of the prior art, Formulation 3.

The term "PDE-4 inhibitor" refers to one or more members of the class of drugs that, when administered to a person, inhibit the enzyme phosphodiesterase-4. Examples of members of this class of drug include apremilast, cilomilast, crisaborole, ibudilast, piclamilast, roflumilast, and rolipram.

The term "roflumilast" as used in this application refers to roflumilast, its salts, the N-oxide of roflumilast, and its salts unless specified otherwise or unless it is clear in context that reference is to roflumilast itself. The terms "N-oxide of roflumilast" and "salts of either roflumilast or of the N-oxide of roflumilast" refer specifically to the N-oxide or salts of either roflumilast or the N-oxide thereof. Roflumilast is described herein, both as a representative member of the class of PDE-4 inhibitors and as roflumilast itself, which includes, depending on context, roflumilast itself, its salts, the N-oxide of roflumilast, and salts of the N-oxide. Roflumilast formulations can be prepared by methods known in the art (e.g. see the '298 patent and U.S. application Ser. No. 14/075,035).

Roflumilast is a compound of the formula (I)

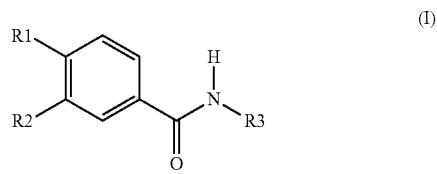

wherein R1 is difluoromethoxy, R2 is cyclopropylmethoxy and R3 is 3,5-dichloropyrid-4-yl.

This compound has the chemical name N-(3,5-dichloropyrid-4-yl)-3-cyclopropylmethoxy-4-difluoromethoxybenzamid- e (INN: roflumilast).

The term "salts", when referring to roflumilast or the N-oxide of roflumilast, means a salt as described in paragraphs [0012] and [0013] of U.S. Patent Application Publication No. US 2006/0084684, the disclosure of which is incorporated herein by reference.

It has been unexpectedly discovered that, in direct contrast to the dogma of the prior art, a pharmaceutical formulation, such as a topically applied pharmaceutical formulation containing a PDE-4 inhibitor, such as roflumilast, provides an altered PK (pharmacokinetic) profile with a reduced Cmax or a reduced absorption rate to reach Cmax when the formulations contain one or more phosphate ester surfactants compared to pharmaceutical formulations containing the PDE-4 inhibitor without a phosphate ester surfactant(s). In particular, it has been unexpectedly discovered that a pharmaceutical formulation containing roflumilast and one or more phosphate ester surfactants, when topically administered to an individual, provides a systemically effective level of the PDE-4 inhibitor comparable to, or even greater than, that achieved with oral administration by slow absorption and without a Cmax spike of the PDE-4 inhibitor into the bloodstream.

In pharmacokinetic terms, a formulation containing a PDE-4 inhibitor drug, such as roflumilast, and a phosphate ester surfactant, when administered to an individual, such as by applying topically to the skin of an individual, provides a sufficiently high Area Under the Curve (AUC) to attain a systemically effective level of the PDE-4 inhibitor drug without rapidly producing a peak plasma concentration (Cmax) that is associated with gastrointestinal side effects. That is, the absorption rate of the drug to reach Cmax is decreased when the formulation of the present application is administered, compared with the administration of formulations of the prior art.

As used herein, the term "absorption rate to reach Cmax" means the slope of the PK curve between the administration of a formulation containing drug until Cmax, or the slope of the PK curve between a trough and the adjacent peak following serial multiple dose administrations of the formulation.

Thus, in contrast to the teachings of the prior art, the formulations of the present application unexpectedly have a markedly different PK profile compared to prior art formulations containing a PDE-4 inhibitor. The formulations of the present application provide a sufficiently high AUC to attain a systemically effective level of the PDE-4 inhibitor without producing a spike in Cmax. The gradual ascent to Cmax obtained following topical application of the formulations of the present invention is markedly different from that of prior art formulations, but the AUC is similar. Additionally, following multiple doses of the formulation, the PK profile lacks the initial Cmax spike and the peak to trough pattern that is obtained following multiple daily dosing with prior art formulations containing the drug.

This discovery provides several unexpected advantages. Primarily, it provides a means for treatment of medical conditions that are responsive to the administration of a PDE-4 inhibitor, that minimizes the incidence of undesirable side effects, especially GI side effects. This in turn leads to greater patient compliance and reduced incidence of cessation of treatment due to the development of such side effects.

Furthermore, because the ascent to Cmax is so slow, and the Cmax spike is avoided, the formulations of the present invention can result in higher systemic exposure levels (AUC) than are possible with prior art formulations and without the side effects associated with Cmax spike, such as those of the G.I. system. Such previously unobtainable exposure levels will provide a greater efficacy in the treatment of diseases.

Moreover, it has been unexpectedly discovered that, following the attainment of Cmax after administration, there is a very flat and prolonged plateau in blood levels of the drug. Additionally, the PK profile obtained after multiple doses of the formulation of the present application is extremely and unexpectedly flat and prolonged with an extremely small peak to trough fluctuation following administration for 28 days. This flatness of the PK profile is especially pronounced when the formulation further contains diethylene glycol monoethyl ether.

Because the absorption of the PDE-4 inhibitor from the formulation in an amount required to provide a therapeutic effect is not dependent on a spike in absorption to provide a high Cmax and because the absorption of the PDE-4 inhibitor is stable and has a flat PK profile, an individual user of the formulation may miss a dose from time to time and still maintain efficacy of the treatment.

An important advantage of the formulations of the present invention is that, because the ascent to Cmax is so slow, and the Cmax spike is avoided, the formulations of the present invention permit the obtaining of higher systemic exposure levels (AUC) than are possible with prior art formulations and without the side effects associated with Cmax spike, such as those of the G.I. system. Such previously unobtainable exposure levels will provide a greater efficacy in the treatment of diseases.

In a first embodiment, the present invention is a pharmaceutical formulation for administering a PDE-4 inhibitor drug to an individual in need thereof.

According to this embodiment, the pharmaceutical formulation of the present invention contains one or more PDE-4 inhibitor drugs. Such PDE-4 inhibitor drugs may include apremilast, cilomilast, crisaborole, ibudilast, piclamilast, roflumilast, and/or rolipram. In a preferred embodiment, the formulation contains roflumilast. The concentration of the PDE-4 inhibitor drug is that which is sufficient to ameliorate a medical condition that is responsive to the administration of a PDE-4 inhibitor drug, such as psoriatic arthritis, psoriasis, atopic dermatitis, asthma and COPD.

The formulation further contains one or more phosphate ester surfactants. Examples of phosphate ester surfactants that may be included in the formulations of this application include but are not limited to potassium cetyl phosphate, potassium C9-15 alkyl phosphate, potassium C11-15 alkyl phosphate, potassium C12-13 alkyl phosphate, potassium C12-14 alkyl phosphate, potassium lauryl phosphate, C8-10 alkyl ethyl phosphate, C9-15 alkyl phosphate, C20-22 alkyl phosphate, castor oil phosphate, ceteth-10 phosphate, cetheth-20 phosphate, ceteth-8 phosphate, cetearyl phosphate, cetyl phosphate, dimethicone PEG-7 phosphate, disodium lauryl phosphate, disodium oleyl phosphate, lauryl phosphate, myristyl phosphate, octyldecyl phosphate, oleth-10 phosphate, oleth-5 phosphate, oleth-3 phosphate, oleyl ethyl phosphate oleyl phosphate, PEG-26-PPG-30 phosphate, PPG-5 ceteareth-10 phosphate, PPG-5 ceteth-10 phosphate, sodium lauryl phosphate, sodium laureth-4 phosphate, steartyl phosphate, DEA-cetyl phosphate, DEA-oleth-10 phosphate, DEA-oleth-3 phosphate, DEA-C8-C18 perfluoroalkylethyl phosphate, dicetyl phosphate, dilaureth-10 phosphate, dimyristyl phosphate, dioleyl phosphate, tricetyl phosphate, triceteareth-4 phosphate, trilaureth-4 phosphate, trilauryl phosphate, triolyeyl phosphate and tristearyl phosphate.

The formulation can optionally contain, in addition to the one or more phosphate ester surfactants, diethylene glycol monoethyl ether. Diethylene glycol monoethyl ether is also known as 2-(2-ethoxyethoxy)ethanol, or as DEGEE, and is marketed under the several tradenames, including TRANSCUTOL® (Gattefosse Corporation, Paramus, NJ), CARBITOL™ (The Dow Chemical Company, Midland, MI), DIOXITOL® (Shell Oil Company, Houston, TX), and POLY-SOLV DM (Monument Chemical, Houston, TX).

DEGEE is often added to topical products as a co-solvent to increase solubility of the drug in the formulation. Addition of DEGEE to a topical formulation has also been shown to enhance skin penetration, i.e. increase Cmax, of topically administered pharmaceutical actives. See Javadzadeh et al, Chapter 12 pages 195-205, in Percutaneous Penetration Enhancers Chemical Methods in Penetration Enhancement: Modification of the Stratum Corneum (N. Dragicevic, H.I. Maibach, eds) Springer-Verlag Berlin Heidelberg 2016.

The concentration of the PDE-4 inhibitor, such as roflumilast, in the formulation is that which is sufficient to obtain a desired systemic pharmacologic effect when the formulation is applied to the skin of an individual. This concentration will necessarily differ based on the particular PDE-4 inhibitor contained within the formulation and the disease or condition to be treated. In the case of roflumilast, the concentration within the formulation is typically in the range of 0.001 to 25% w/w, with a preferred range between 0.01 to 5%, a more preferred range between 0.05 and 1%, and a most preferred range between 0.1 and 0.5%. In a particular preferred embodiment, the concentration of roflumilast in the formulation is between 0.05 and 0.5%, such as 0.05%, 0.15%, 0.3%, and 0.5% w/w.

The concentration of the phosphate ester surfactant in the formulation is that which is sufficient to produce a stable emulsion having uniform globule size. If desired, lower concentrations of the phosphate ester surfactant may be combined with other emulsifiers to produce a stable emulsion having uniform globule size. The phosphate ester surfactant may also increase the solubility of the roflumilast in the cream. The concentration of the phosphate ester surfactant generally may be any concentration between 1.0% to 25% w/w. The preferred concentration can be different for different administration forms. In a preferred embodiment, when the formulation is a cream or ointment, the concentration of the phosphate ester surfactant is between 2.5% and 20%, with a more preferred concentration range between 5% and 15%, and a most preferred concentration being about 10% w/w. When the formulation is in the form of a foam, the concentration is preferably between 1.0%-10%, more preferably between 1.0%-10%, and most preferably 2%.

The concentration of the diethylene glycol monoethyl ether, if present, in the formulation is that which is sufficient to dissolve the active pharmaceutical ingredient. Diethylene glycol monoethyl ether may also enhance the skin penetration of the roflumilast. Generally, the concentration of the diethylene glycol monoethyl ether is between 5% and 50% w/w, with a preferred range of concentrations between 10% and 40% w/w, a more preferred range between 15% and 30% w/w, and a particular preferred concentration being about 15-25% w/w. Likewise, water is formulated as about 20-90% (w/w) in topical products. For blends of DEGEE and water the ratio can range from 1:10 to 20:1. Preferably the DEGEE:water ratio is 1:4 to 9:1 in a formulation containing roflumilast. Generally, DEGEE-water blends can be used to dissolve up to 2.0% roflumilast (in the finished product) or preferably up to 0.5% roflumilast (in the finished product).

The formulation for topical application to the skin is preferably a semi-solid dosage form that is cosmetically acceptable for use on the skin and which is easily spreadable on the skin. Examples of such semi-solid dosage forms include emulsions, ointments, creams, gels, and pastes. The formulation may alternatively be in a form other than a semi-solid dosage form, such as a liquid, which may be administered as a spray, or a foam. Preferably, a formulation for topical administration is in one of the following forms:

An oil-in-water emulsion: The topical product may be an emulsion comprising a discrete hydrophobic phase and a continuous aqueous phase that includes the DEGEE-water blend and optionally one or more polar hydrophilic excipients as well as solvents, co-solvents, salts, surfactants, emulsifiers, and other components. These emulsions may include water-soluble or water-swellable polymers that help to stabilize the emulsion.

A water-in-oil emulsion: The compositions may be formulations in which roflumilast is incorporated into an emulsion that includes a continuous hydrophobic phase and an aqueous phase that includes the DEGEE-water blend and optionally one or more polar hydrophilic carrier(s) as well as salts or other components. These emulsions may include oil-soluble or oil-swellable polymers as well as one or more emulsifier(s) that help to stabilize the emulsion.

For both oil-in-water and water-in-oil emulsions, order of addition may be important. Roflumilast can be added predissolved in the continuous aqueous phase containing the DEGEE-water blend. Likewise, roflumilast can be predissolved in the hydrophobic discrete phase of the emulsion that is then mixed with the DEGEE-water blend and optional hydrophilic excipients that do not contain the active ingredient. Roflumilast can be pre-dissolved in both the oil phase and water phase of the emulsion or added pre-dissolved in DEGEE or a DEGEE-water blend after the emulsion has been formed. Some emulsions undergo phase inversion over a specific temperature range during cooling of the emulsion. Thus, roflumilast may be added to a water-in-oil emulsion above the phase inversion temperature, with the final drug product being an oil-in-water emulsion at controlled room temperature, or vice versa.

Thickened aqueous gels: These systems include the DEGEE-water blend with dissolved roflumilast and optionally one or more polar hydrophilic carrier(s) such as hexylene glycol which has been thickened by suitable natural, modified natural, or synthetic thickeners as described below. Alternatively, the thickened aqueous gels can be thickened using suitable polyethoxylate alky chain surfactants or other nonionic, cationic, or anionic systems.

Thickened hydroalcoholic gels: These systems include the DEGEE-water-alcohol blend with dissolved roflumilast and optionally one or more polar hydrophilic carrier(s) such as hexylene glycol as the polar phase which has been thickened by suitable natural, modified natural, or synthetic polymers such as described below. Alternatively, the thickened hydroalcoholic gels can be thickened using suitable polyethoxylate alky chain surfactants or other nonionic, cationic, or anionic systems. The alcohol can be ethanol, isopropyl alcohol or other pharmaceutically acceptable alcohol.

A hydrophilic or hydrophobic ointment: The compositions are formulated with a hydrophobic base (e.g. petrolatum, thickened or gelled water insoluble oils, and the like) and optionally have a minor amount of the DEGEE-water blend with dissolved roflumilast. Hydrophilic ointments generally contain one or more surfactants or wetting agents.

In addition to the PDE-4 inhibitor, such as roflumilast, and phosphate ester surfactant, with or without the optional diethylene glycol monoethyl ether, the formulation may contain additional excipients commonly present in such dosage forms. Such excipients will vary depending on the type of the dosage form and the desired characteristics.

Solvents

Compositions of the present invention may include one or more solvents or co-solvents to obtain the desired level of active ingredient solubility in the product. The solvent may also modify skin permeation or activity of other excipients contained in a topical product. Solvents include but are not limited to acetone, ethanol, benzyl alcohol, butyl alcohol, diethyl sebacate, diethylene glycol monoethyl ether, diisopropyl adipate, dimethyl sulfoxide, ethyl acetate, isopropyl alcohol, isopropyl isostearate, isopropyl myristate, N-methyl pyrrolidinone, propylene glycol and SD alcohol.

Moisturizers

Compositions of the present invention may include a moisturizer to increase the level of hydration. For emulsions, the moisturizer is often a component of the discrete or continuous hydrophobic phase. The moisturizer can be a hydrophilic material including humectants or it can be a hydrophobic material including emollients. Suitable moisturizers include but are not limited to: 1,2,6-hexanetriol, 2-ethyl-1,6-hexanediol, butylene glycol, glycerin, polyethylene glycol 200-8000, butyl stearate, cetostearyl alcohol, cetyl alcohol, cetyl esters wax, cetyl palmitate, cocoa butter, coconut oil, cyclomethicone, dimethicone, docosanol, ethylhexyl hydroxystearate, fatty acids, glyceryl isostearate, glyceryl laurate, glyceryl monostearate, glyceryl oleate, glyceryl palmitate, glycol distearate, glycol stearate, isostearic acid, isostearyl alcohol, lanolin, mineral oil, light mineral oil, lanolin, limonene, medium-chain triglycerides, menthol, myristyl alcohol, octyldodecanol, oleic acid, oleyl alcohol, oleyl oleate, olive oil, paraffin, peanut oil, petrolatum, Plastibase-50W, sorbitol, stearic acid, stearyl alcohol, and urea.

Surfactants and Emulsifiers

Compositions according to the present invention can optionally include one or more surfactants to emulsify the composition and to help wet the surface of the active ingredients or excipients. As used herein the term "surfactant" means an amphiphile (a molecule possessing both polar and nonpolar regions which are covalently bound) capable of reducing the surface tension of water and/or the interfacial tension between water and an immiscible liquid. Surfactants include but are not limited to alkyl aryl sodium sulfonate, Amerchol-CAB, ammonium lauryl sulfate, apricot kernel oil PEG-6 esters, Arlacel, benzalkonium chloride, Ceteareth-6, Ceteareth-12, Ceteareth-15, Ceteareth-30, cetearyl alcohol/ceteareth-20, cetearyl ethylhexanoate, ceteth-10, ceteth-10 phosphate, ceteth-2, ceteth-20, ceteth-23, choleth-24, cocamide ether sulfate, cocamine oxide, coco betaine, coco diethanolamide, coco monoethanolamide, coco-caprylate/caprate, dicetyl phosphate, disodium cocoamphodiacetate, disodium laureth sulfosuccinate, disodium lauryl sulfoacetate, disodium lauryl sulfosuccinate, disodium oleamido monoethanolamine sulfosuccinate, docusate sodium, laureth-2, laureth-23, laureth-4, lauric diethanolamide, lecithin, mehoxy PEG-16, methyl gluceth-10, methyl gluceth-20, methyl glucose sesquistearate, oleth-2, oleth-20, PEG 6-32 stearate, PEG-100 stearate, PEG-12 glyceryl laurate, PEG-120 methyl glucose dioleate, PEG-15 cocamine, PEG-150 distearate, PEG-2 stearate, PEG-20 methyl glucose sesqustearate, PEG-22 methyl ether, PEG-25 propylene glycol stearate, PEG-4 dilaurate, PEG-4 laurate, PEG-45/dodecyl glycol copolymer, PEG-5 oleate, PEG-50 Stearate, PEG-54 hydrogenated castor oil, PEG-6 isostearate, PEG-60 hydrogenated castor oil, PEG-7 methyl ether, PEG-75 lanolin, PEG-8 laurate, PEG-8 stearate, Pegoxol 7 stearate, pentaerythritol cocoate, poloxamer 124, poloxamer 181, poloxamer 182, poloxamer 188, poloxamer 237 poloxamer 407, polyglyceryl-3 oleate, polyoxyethylene alcohols, polyoxyethylene fatty acid esters, polyoxyl 20 cetostearyl ether, polyoxyl 40 hydrogenated castor oil, polyoxyl 40 stearate, polyoxyl 6 and polyoxyl 32, polyoxyl glyceryl stearate, polyoxyl stearate, polysorbate 20, polysorbate 40, polysorbate 60, polysorbate 65, polysorbate 80, PPG-26 oleate, PROMULGENTM 12, propylene glycol diacetate, propylene glycol dicaprylate, propylene glycol monostearate, sodium xylene sulfonate, sorbitan monooleate, sorbitan monopalmitate, sorbitan monostearate, steareth-2, steareth-20, steareth-21, steareth-40, tallow glycerides, and emulsifying wax.

Suitable phosphate ester surfactants include but are not limited to potassium cetyl phosphate, potassium C9-15 alkyl phosphate, potassium C11-15 alkyl phosphate, potassium C12-13 alkyl phosphate, potassium C12-14 alkyl phosphate, potassium lauryl phosphate, C8-10 alkyl ethyl phosphate, C9-15 alkyl phosphate, C20-22 alkyl phosphate, castor oil phosphate, ceteth-10 phosphate, ceteth-20 phosphate, ceteth-8 phosphate, cetearyl phosphate, cetyl phosphate, dimethicone PEG-7 phosphate, disodium lauryl phosphate, disodium oleyl phosphate, lauryl phosphate, myristyl phosphate, octyldecyl phosphate, oleth-10 phosphate, oleth-5 phosphate, oleth-3 phosphate, oleyl ethyl phosphate oleyl phosphate, PEG-26-PPG-30 phosphate, PPG-5 cetearth-10 phosphate, PPG-5 ceteth-10 phosphate, sodium lauryl phosphate, sodium laureth-4 phosphate, steartyl phosphate, DEA-cetyl phosphate, DEA-oleth-10 phosphate, DEA-oleth-3 phosphate, DEA-C8-C18 perfluoroalkylethyl phosphate, dicetyl phosphate, dilaureth-10 phosphate, dimyristyl phosphate, dioleyl phosphate, tricetyl phosphate, triceteareth-4 phosphate, trilaureth-4 phosphate, trilauryl phosphate, triolyeyl phosphate and tristearyl phosphate.

Polymers and Thickeners

For certain applications, it may be desirable to formulate a topical product that is thickened with soluble, swellable, or insoluble organic polymeric thickeners such as natural and synthetic polymers or inorganic thickeners including but not limited to acrylates copolymer, carbomer 1382, carbomer copolymer type B, carbomer homopolymer type A, carbomer homopolymer type B, carbomer homopolymer type C, caroboxy vinyl copolymer, carboxymethylcellulose, carboxypolymethylene, carrageenan, guar gum, hydroxyethyl cellulose, hydroxypropyl cellulose, microcrystalline wax, and methylcellulose.

The formulation may contain one or more thickening agent to provide viscosity so that the formulation may be provided in the form of a semisolid, such as a lotion, gel, cream, or ointment. Examples of suitable thickening agents include but are not limited to soluble, swellable, or insoluble organic polymeric thickeners such as natural and synthetic polymers or inorganic thickeners including but not limited to acrylates copolymer, carbomer 1382, copolymer type B, carbomer homopolymer type A, homopolymer type B, carbomer homopolymer type C, carboxypolymethylene, carrageenan, guar gum, hydroxyethyl cellulose, hydroxypropyl cellulose, microcrystalline wax, acacia, alginic acid, bentonite, carbomers, also known as carboxy vinyl polymers, such as sold under the tradename Carbopol® (Lubrizol, Wickliffe, Ohio), carboxymethylcellulose, ethylcellulose, gelatin, hydroxyethylcellulose, hydroxypropyl cellulose, magnesium aluminum silicate, methylcellulose, poloxamers, polyvinyl alcohol, sodium alginate, tragacanth, and xanthan gum. The thickening agent may reside in the oil or lipophilic portion of the formulation. Examples of suitable lipophilic thickening agents include cetyl alcohol, stearyl alcohol, glyceryl stearate, white beeswax, microcrystalline wax, hydrogenated polyisobutane polymers, and emulsifying wax.

Additional Components

Compositions according to the present invention may be formulated with additional components such as fillers, carriers and excipients conventionally found in cosmetic and pharmaceutical topical products. Additional components include but are not limited to foaming agents, propellants, preservatives, antioxidants, sequestering agents, stabilizers, buffers, pH adjusting solutions, skin penetration enhancers, chelating agents, film formers, dyes, pigments, fragrances and other excipients to improve the stability or aesthetics of the product. In a preferred embodiment, hexylene glycol is added to inhibit changes in particle size distribution over the shelf life of the composition. Hexylene glycol can be added between 0.1% and 20% on a weight/weight basis, preferably between 0.25% and 8% on a weight/weight basis and most preferably between 0.5% and 2% on a weight/weight basis.

The formulation may contain other pharmaceutically acceptable excipients if desired. For example, the formulation may contain a humectant such as glycerin, sorbitol, hexylene glycol, urea, or propylene glycol. The formulation may contain an emollient such as petrolatum, lanolin, mineral oil, light mineral oil, stearic acid, cyclomethicone, or dimethicone. Additional optional excipients include stabilizers, foaming agents, preservatives such as methylparaben, pH adjusting agents such as sodium hydroxide, chelating agents such as EDTA and its salts, and buffers.

In one preferred embodiment, the roflumilast is in the form of an aerosolized foam which is particularly suitable for application to the scalp. Any suitable propellant can be used to prepare the aerosolized foam. Particularly preferred propellants are Isobutane A-31, Aeropin 35, Butane 48, Dimethyl Ether/N-Butane-(53/47), Propane/Iso-Butane/N-Butane, Propane/Isobutane-A70, and Propane/Isobutane A-46, N-Butane (A-17.

Additional Active Agents

Compositions according to the present invention may be formulated with additional active agents depending on the condition to be treated. The additional active agents include but are not limited to NSAIDs (e.g. Aspirin, Ibuprofen, Ketoprofen, Naproxen), Apremilast, JAK inhibitors (e.g. Tofacitinib, Ruxolitinib, Oclacit), leukotriene inhibitors (e.g. Zileuton, Zafirlukast, Montelukast), mast cell stabilizers (e.g. Nedocromil, Cromolyn sodium, Ketotifen, Pemirolast), Anthralin (dithranol), Azathioprine, Tacrolimus, Coal tar, Methotrexate, Methoxsalen, Salicylic acid, Ammonium lactate, Urea, Hydroxyurea, 5-fluorouracil, Propylthouracil, 6-thioguanine, Sulfasalazine, Mycophenolate mofetil, Fumaric acid esters, Corticosteroids (e.g. Aclometasone, Amcinonide, Betamethasone, Clobetasol, Clocotolone, Mometasone, Triamcinolone, Fluocinolone, Fluocinonide, Flurandrenolide, Diflorasone, Desonide, Desoximetasone, Dexamethasone, Halcinonide, Halobetasol, Hydrocortisone, Methylprednisolone, Prednicarbate, Prednisone), Corticotropin, Vitamin D analogues (e.g. calcipotriene, calcitriol), Acitretin, Tazarotene, Cyclosporine, Resorcinol, Colchicine, bronchodialators (e.g. beta-agonists, anticholinergics, theophylline), and antibiotics (e.g. erythromycin, ciprofloxacin, metronidazole).

Administration and Dosage

Suitable pharmaceutical dosage forms include but are not limited to emulsions, suspensions, sprays, oils, ointments, fatty ointments, creams, pastes, gels, foams transdermal patches, and solutions.

The composition preferably contains roflumilast, salts of roflumilast, the N-oxide of roflumilast or salts thereof in an amount of 0.005-2% w/w, more preferably 0.05-1% w/w, and most preferably 0.1-0.5% w/w per dosage unit. The topical formulation containing the PDE-4 inhibitor, such as roflumilast, is applied to the skin in an amount that is sufficient to obtain the desired pharmacologic effect, which typically is to ameliorate the signs and/or symptoms of a medical disorder. The amount of the formulation that is applied may vary depending on the PDE-4 inhibitor that is contained within the formulation, the concentration of the PDE-4 inhibitor within the formulation, and the frequency in which the formulation is applied. Generally, the formulation is applied with a frequency between weekly to several times daily, preferably between every other day to three times daily, and most preferably one or two times daily.

The formulation containing the PDE-4 inhibitor may be used in veterinary and in human medicine to treat a systemic medical condition that is ameliorated by or responsive to systemic administration of a PDE-4 inhibitor such as roflumilast. Non-limiting examples of such medical conditions include but are not limited to acute and chronic airway disorders such as bronchitis, allergic bronchitis, asthma, and COPD; proliferative, inflammatory and allergic dermatoses such as psoriasis, scalp psoriasis, or inverse psoriasis, irritant and allergic contact eczema, hand eczema, atopic dermatitis, seborrheic dermatitis, lichen simplex, sunburn, aphthous ulcers, lichen planus, vitiligo, pruritus in the genital or anal regions, alopecia areata, hypertrophic scars, discoid lupus erythematosus, follicular and extensive pyodermas, endogenous and exogenous acne, acne rosacea, disorders which are based on an excessive release of TNF and leukotrienes, disorders of the heart which can be treated by PDE inhibitors, inflammations in the gastrointestinal system or central nervous system, disorders of the eye, disorders which can be treated by the tissue-relaxant action of PDE inhibitors and other proliferative, inflammatory and allergic skin disorders; and immune mediated diseases such as arthritis including rheumatoid arthritis, rheumatoid spondylitis, osteoarthritis, and psoriatic arthritis.

The formulation for topical application containing the PDE-4 inhibitor, such as roflumilast, may be prepared by processes typically used in the field of manufacture of pharmaceutical formulations for topical application. In order to make a single-phase formulation, such as a liquid, the constituents of the formulation may be combined and mixed until a homogenous solution or suspension of the active ingredient is obtained. In order to make a multiphase formulation such as an emulsion, for example, the components of the aqueous phase and of the oil phase may be separately combined and mixed until homogenous solutions are obtained and then the aqueous solution and the oil solution may be combined and mixed, such as by shear mixing, to form the formulation. The one or more drug actives may be dissolved (molecularly dispersed), complexed, or associated with an excipient or other active, or may be particulate (amorphous or crystalline). The oil phase may be added to the water phase, or the water phase may be added to the oil phase. The phases may be combined and mixed, such as at elevated temperatures of 50-90° C. or at room temperature, that is between 20-30° C., or at a temperature between room temperature and the elevated temperatures.

The following examples are provided to enable those of ordinary skill in the art to make and use the methods and compositions of the invention. These examples are not intended to limit the scope of what the inventors regard as their invention. Additional advantages and modifications will be readily apparent to those skilled in the art.

In the following examples roflumilast is utilized as a representative example of a PDE-4 inhibitor drug. Also, in the following examples, Crodafos™ CES (Croda Inc., Edison, NJ), containing the phosphate ester surfactants dicetyl phosphate and ceteth-10 phosphate, is utilized as a representative example of a phosphate ester surfactant.

Example 1—Formulations According to the Invention and of the Prior Art

A first formulation of the invention, hereafter referred to as Formulation 1, was made by combining roflumilast with a phosphate ester surfactant and water. The formulation was buffered with NaOH to obtain a pH of 6.5.

A second formulation of the invention, hereafter referred to as Formulation 2, was made by combining the above constituents and adding diethylene glycol monoethyl ether. This formulation was buffered with NaOH to obtain a pH of 6.5.

A formulation that is not of the invention, hereafter referred to as Comparative Formulation 3, was made by combining roflumilast with diethylene glycol monoethyl ether. This formulation was gelled with hydroxylpropyl cellulose so that it would have a similar viscosity and spread on the skin like the two phosphate ester surfactant emulsion Formulations 1, and 2. This semisolid formulation was likewise buffered with NaOH to obtain a pH of 6.5.

The compositions of these formulations are shown below in Table 1.

TABLE 1

| | Formulation 1 | Formulation 2 | Comparative Formulation 3 |
|---|---|---|---|
| Roflumilast | 0.15% w/w | 0.15% w/w | 0.15% w/w |
| Crodafos CES cetostearyl alcohol dicetyl phosphate ceteth-10 phosphate | 10.0% w/w | 10.0% w/w | |
| Diethylene Glycol Monoethyl Ether, NF | | 25.0% w/w | 25.0% w/w |
| Hydroxypropyl Cellulose | | | 0.5% w/w |
| 1N NaOH, NF | q.s. ad pH 6.5 | q.s. ad pH 6.5 | q.s. ad pH 6.5 |
| Purified Water, USP | q.s. ad 100% | q.s. ad 100% | q.s. ad 100% |

Example 2—Single Dose Testing of Formulations of Example 1

Male and female swine (Gottingen Minipig® breed) (Marshall BioResources, North Rose, NY) were ordered to weigh 8 to 12 kg at arrival. On the day prior to administration of one of the topical cream semisolid formulations of Example 1 containing 0.15% roflumilast, the hair was clipped from the back of each animal. The pigs were sedated for the shaving procedure. Care was taken to avoid abrading the skin.

Two (2) grams of one of the cream formulations of Example 1 for each kg of pig weight was distributed over the clipped skin area by gentle inunction with a glass stirring rod or stainless-steel spatula. The cream formulation was applied evenly with a thin, uniform film beginning at the scapular region and moving caudally over the test site. The width of the test site area was bilaterally divided by the spine. Six pigs (3 males and 3 females) were administered a single dose of the Formulation 2. Blood was sampled from the anterior vena cava through the thoracic inlet or other suitable vein pre-dose (time=0) and at 1, 2, 4, 8 and 24 hours post dose administration. A one-week wash out (no product dosed) was sufficient to reduce plasma levels of roflumilast to zero as verified by the pre-dose (time=0) sample. After the wash out period, a single dose of formulation 1 was applied. After a second one-week wash out period, a single dose of Formulation 3 was applied. Blood samplings were the same for all three groups. The results are shown graphically in FIG. 1.

As shown in FIG. 1, pigs dosed with Comparative Formulation 3 of the prior art showed a rapid spike to Cmax within 3 hours of dosing. In contrast, pigs dosed with Formulation 1 of the invention containing the phosphate ester surfactant Crodafos CES showed little or no spike to Cmax. Pigs dosed with Formulation 2 of the invention containing both a phosphate ester surfactant and diethylene glycol monoethyl ether, like those dosed with Formulation 1, showed a reduced spike to Cmax as compared to Formulation 3. However, the higher Cmax obtained with Formulation 2 was higher than that for Formulation 1.

The PK data results in the graph of FIG. 1 show that the single dose PK profile data for the formulation containing phosphate ester surfactants lacks a significant spike to Cmax and has a low Cmax of 0.36 ng/mL, while maintaining a mean plasma concentration of 0.34 ng/ml through the 4 hour sample point. This is in contrast to PK data for the DEGEE formulation that rapidly raises to a Cmax of 0.85 ng/ml at 2 hours and then just as quickly drops to 0.57 ng/mL at 4 hours. When the phosphate ester surfactant is added to DEGEE the formulation of the invention, it lacks a significant spike to Cmax and has a low Cmax, while maintaining AUC, in contrast to PK data for the DEGEE formulation which does not contain phosphate ester surfactants. This PK data is especially surprising in view of the fact that the prior art (Bolle) teaches that Cmax and AUC are similar for topical preparations containing roflumilast, irrespective of the composition of the topical formulation. In contrast to what one would expect based on the teachings of the prior art, Formulation 1, containing phosphate ester surfactant, lacks a significant spike to Cmax. Moreover, the mean plasma concentration of 0.34 ng/ml was maintained throughout the 4 hour sample point. In contrast, Formulation 3 containing diethylene glycol monoethyl ether but lacking a phosphate ester surfactant, showed a rapid spike rise to Cmax of 0.85 ng/ml at two hours. When a phosphate ester surfactant was utilized in combination with diethylene glycol monoethyl ether, Formulation 2 administration produced no significant spike to Cmax and had a Cmax between those obtained with Formulations 1 and 3, while maintaining AUC.

Example 3—Formulation of the Invention and a Formulation of the Closest Prior Art A third embodiment of the invention, hereafter referred to as Formulation 4, was made by combining roflumilast at a concentration of 0.3% w/w with a phosphate ester surfactant and water. The formulation was buffered with NaOH to obtain a pH of 5.5. This formulation is similar to Formulation 1 except that the concentration of roflumilast is 0.3% rather than 0.15% and the emulsion is buffered to a pH value of 5.5 rather than a pH value of 6.5.

A formulation that is not of the invention, hereafter referred to as Comparative Formulation 5, was made by combining roflumilast at a concentration of 0.3% containing a phosphate ester surfactant, a polyoxyl stearyl ether surfactant and diethylene glycol monoethyl ether, as well as other excipients. This formulation is a cream formulation containing a frequently used phosphate ester surfactant that is not Crodafos CES.

A formulation that is not of the invention, hereafter referred to as Comparative Formulation 6, was made by combining roflumilast at a concentration of 0.2%. This formulation is that of the closest prior art known to the inventors and is disclosed in Example 3 of Bolle et al, U.S. Patent Application No. US 2006/0084684.

The compositions of these formulations are shown below in Table 2.

TABLE 2

|  | Formulation 4 | Comparative Formulation 5 | Comparative Formulation 6 |
|---|---|---|---|
| Roflumilast | 0.3% w/w | 0.3% w/w | 0.2% w/w |
| Petrolatum, USP | — | 10.0% w/w | — |
| Isopropyl Palmitate, NF | — | 5.0% w/w | — |
| Medium-Chain Triglycerides | — | — | 25.0% w/w |
| Crodafos CES | 10.0% w/w | — | — |
| cetostearyl alcohol | (6-8% w/w) | | |
| dicetyl phosphate | (1-2% w/w) | | |
| ceteth-10 phosphate | (1-2% w/w) | | |
| Potassium Cetyl Phosphate | | 2.0% w/w | |
| Cetostearyl Alcohol | | 6.0% w/w | 5.0% w/w |
| Polyoxyl Stearyl Ether | | 2.0% w/w | |
| Glyceryl Stearate/PEG-100 Stearate | | — | 5.0% w/w |
| Diethylene Glycol Monoethyl Ether, NF | — | 25.0% w/w | — |
| Hexylene Glycol, NF | — | 2.0% w/w | — |
| Methylparaben, NF | — | 0.20% w/w | — |
| Propylparaben, NF | — | 0.050% w/w | — |
| 1N NaOH, NF | q.s. ad pH 5.5 | q.s. ad pH 5.5 | — |
| Purified Water, USP | q.s. ad 100% | q.s. ad 100% | q.s. ad 100% |

*The exact ratio of cetostearyl alcohol to dicetyl phosphate to ceteth-10 phosphate in Crodafos CES is consistent between batches of product but is not publicly disclosed by the manufacturer (Croda). The safety data sheet for Crodafos CES states that this emulsifier is composed of 60-80% cetostearyl alcohol, 10-20% dicetyl phosphate and 10-20% ceteth-10 phosphate. To emphasize the similarity in composition between Formulation 4 (phosphate-ester surfactant blend) and Comparative Formulation 5 (phosphate ester and nonionic surfactant blend) and Comparative Formulation 6 (nonionic surfactant blend), the cetostearyl alcohol portion of Crodafos CES is listed separately from the surfactant portion of Crodafos CES in Table 2.
Glyceryl Stearate/PEG-100 Stearate is the nomenclature used by the US Food and Drug Administration to describe the nonionic emulsifier blend sold using the tradename Arlacel® 165 and Tego Care® 150.
Medium-Chain Triglycerides is the nomenclature used by the US Food and Drug Administration to describe the cosmetic ingredient Capryli/Capric Triglyceride which is sold using tradenames including Miglyol® 812 and Crodamol® GTCC.

Example 4-14-Day Dose Testing of Formulations of Example 3

Male and female swine (Gottingen Minipig® breed) are ordered to weigh 8 to 12 kg at arrival. On the day prior to administration of one of the topical cream semisolid formulations of Example 3, the hair is clipped from the back of each animal. The pigs are sedated for the shaving procedure. Care is taken to avoid abrading the skin.

Two (2) grams of one of the cream formulations of Example 3 for each kg of pig weight is distributed over the clipped skin area by gentle inunction with a glass stirring rod or stainless-steel spatula. The cream formulation is applied evenly with a thin, uniform film beginning at the scapular region and moving caudally over the test site. The width of the test site area is bilaterally divided by the spine. Eighteen pigs are divided into 3 groups of six pigs (3 males and 3 females) and the pigs of each group were dosed with one of the formulations 4, 5, or 6. Blood is sampled from the anterior vena cava through the thoracic inlet or other suitable vein pre-dose (time=0) and at 1, 2, 4, 8 and 24 hours post dose administration. The results are shown graphically in FIG. 2.

Figure 2:
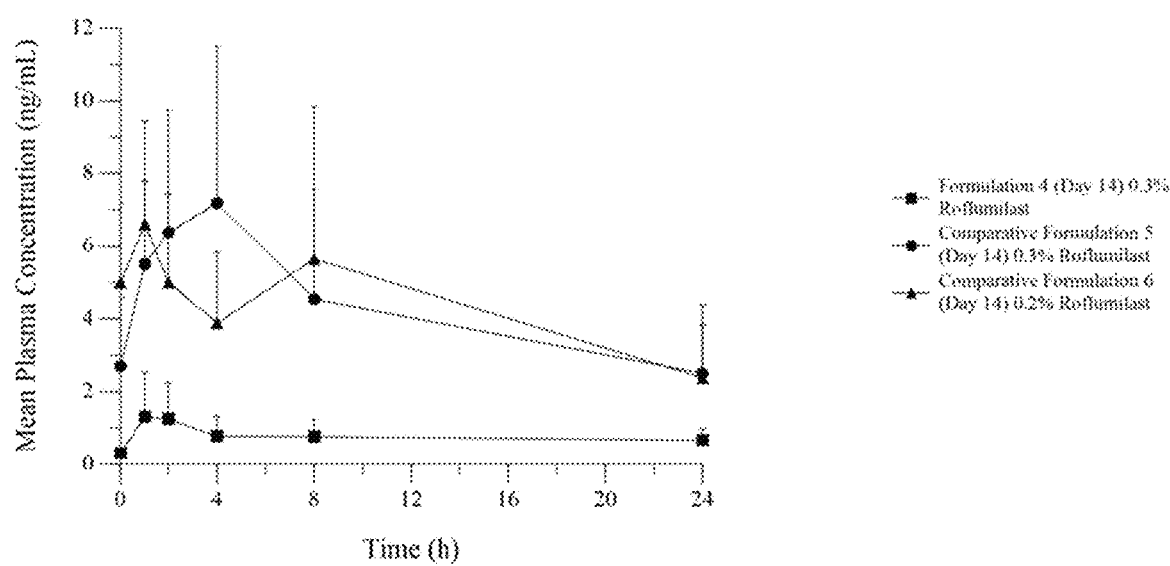
FIG. 2 is a graph comparing the slow rise to Cmax of Formulation 4 (dicetyl phosphate/ceteth-10 phosphate) with the significantly greater roflumilast Cmax peak values (compared to trough T=0 plasma concentrations) following dosing with comparative formulation 5 (potassium cetyl phosphate) and comparative formulation 6 (Cetostearyl Alcohol and Glyceryl Stearate/PEG-100 Stearate).

As shown in FIG. 2, pigs dosed with Formulation 5 of the prior art show a rapid spike to a Cmax value of 6.6 ng/mL at 1 hour after the $14^{th}$ consecutive daily dose. In contrast, pigs dosed with Formulation 4 of the invention containing the phosphate ester surfactant Crodafos CES show little or no spike to Cmax.

The results show in the graph of FIG. 2, that the steady state PK profile data after 14 days of once daily dosing for the formulation of the invention lacks a significant spike to Cmax and has a low Cmax, while maintaining AUC, in contrast to PK data for the prior art formulation or a formulation using a phosphate ester surfactant that was not Crodafos CES. These results are especially surprising in view of the fact that the prior art (Bolle) teaches that Cmax and AUC are similar for topical preparations containing roflumilast, irrespective of the composition of the topical formulation.

Example 5—Testing for Multiple Dose Pharmacokinetics Compared to Prior Art

A fourth formulation of the invention is shown in Table 3, hereafter referred to as Formulation 7, was made by combining the above constituents and adding diethylene glycol monoethyl ether, as well as other ingredients to create a complete formulation. This formulation was buffered with NaOH to obtain a pH of 5.5. The qualitative and quantitative composition of Formulation 7 varies only in the amount of roflumilast added to the cream. As a fraction of 1% roflumilast is added, a fraction of 1% of water is removed from the cream.

TABLE 3

| Formulation 7 | |
|---|---|
| Roflumilast | 0.15, 0.3, 0.5 or 1.0% w/w |
| Petrolatum, USP | 10.0% w/w |
| Isopropyl Palmitate, NF | 5.0% w/w |
| Crodafos CES | 10.0% w/w |
| cetostearyl alcohol | (6-8% w/w) |
| dicetyl phosphate | (1-2% w/w) |
| ceteth-10 phosphate | (1-2% w/w) |
| Diethylene Glycol Monoethyl Ether, NF | 25.0% w/w |
| Hexylene Glycol, NF | 2.0% w/w |
| Methylparaben, NF | 0.20% w/w |
| Propylparaben, NF | 0.050% w/w |
| 1N NaOH, NF | q.s. ad pH 5.5 |
| Purified Water, USP | q.s. ad 100% |

Male and female swine (Gottingen Minipig® breed) were ordered to weigh 8 to 12 kg at arrival. On the day prior to administration of a topical cream containing roflumilast, the hair was clipped from the back of each animal. The pigs were sedated for the shaving procedure. Care was taken to avoid abrading the skin.

Figure 3:
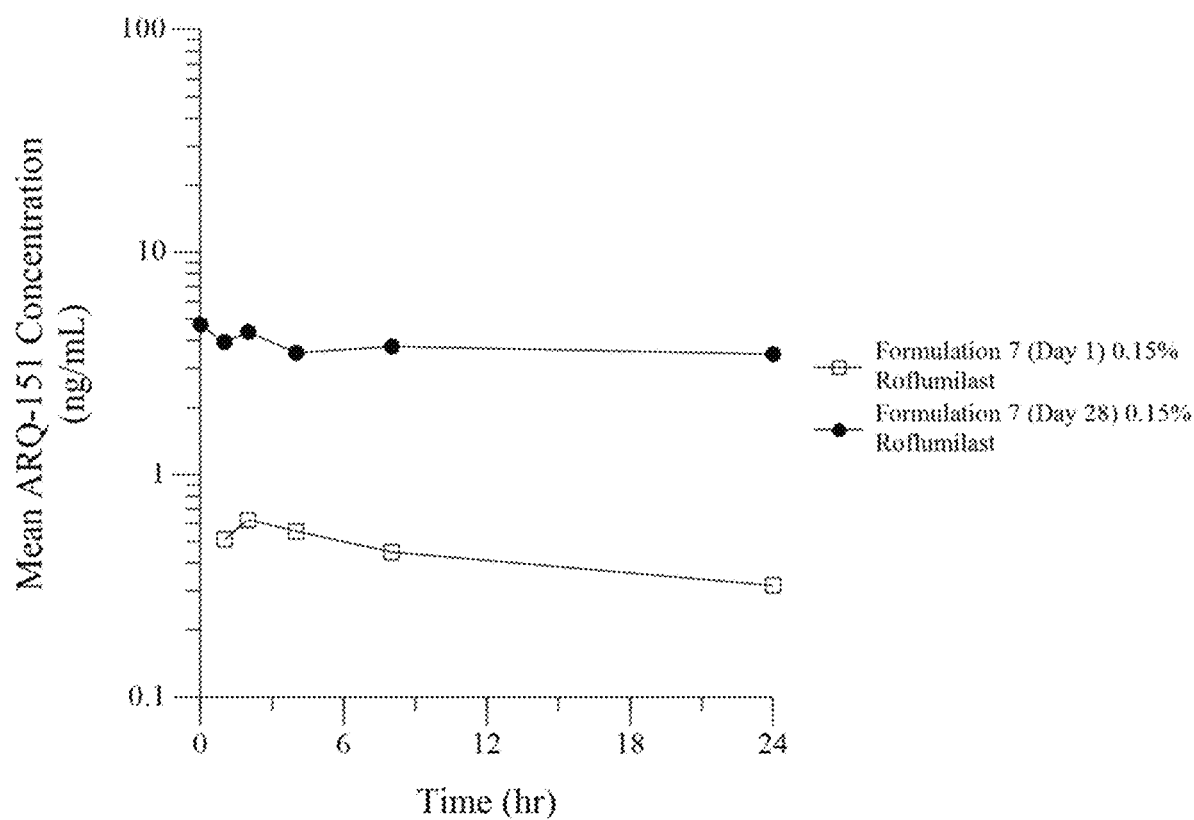
FIG. 3 is a line graph showing Day 1 and Day 28 PK profiles after once daily dosing of 0.15% roflumilast topical cream.
Figure 4:
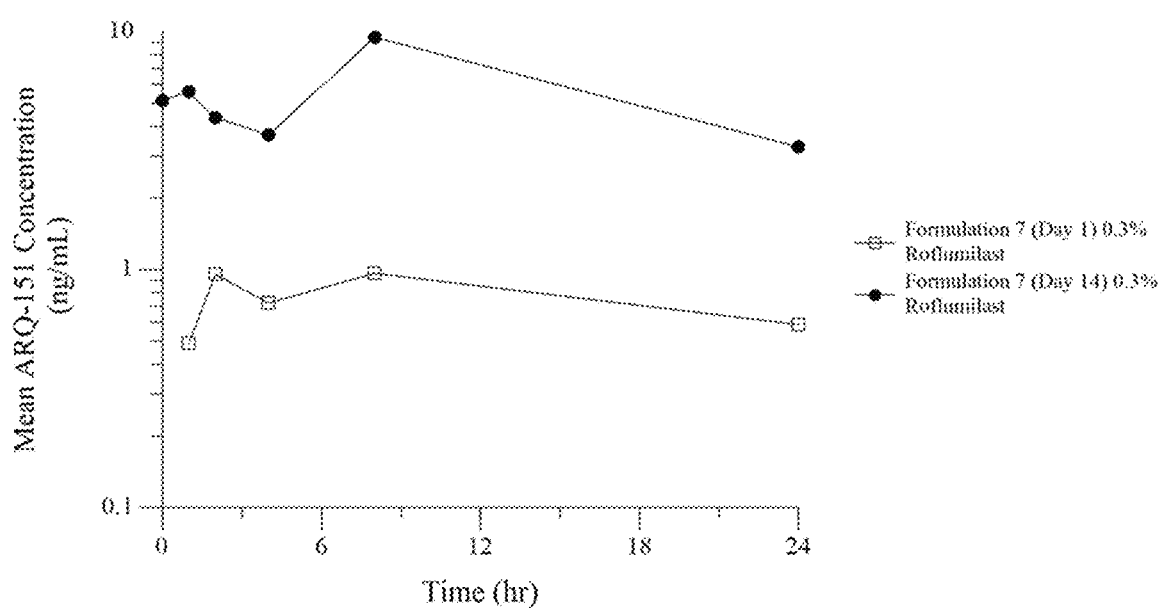
FIG. 4 is a line graph showing Day 1 and Day 14 PK profiles after once daily dosing of 0.3% roflumilast topical cream.
Figure 5:
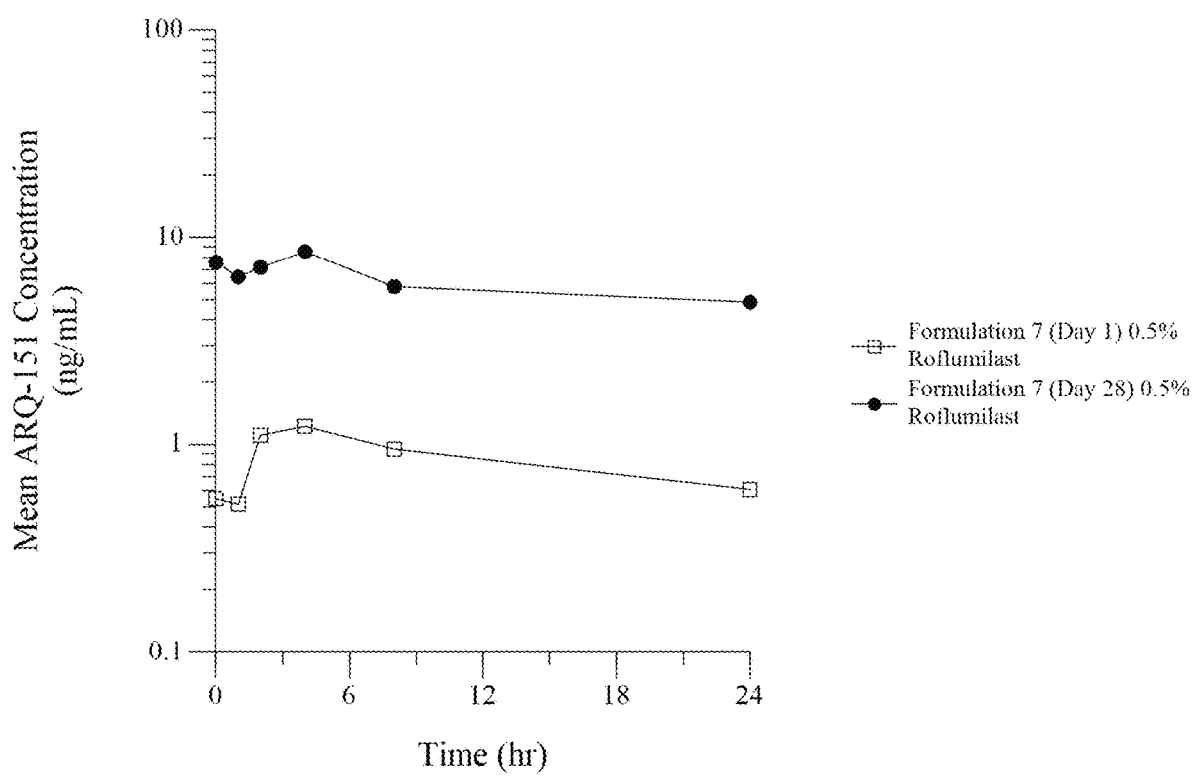
FIG. 5 is a line graph showing Day 1 and Day 28 PK profiles after once daily dosing of 0.5% roflumilast topical cream.
Figure 6:
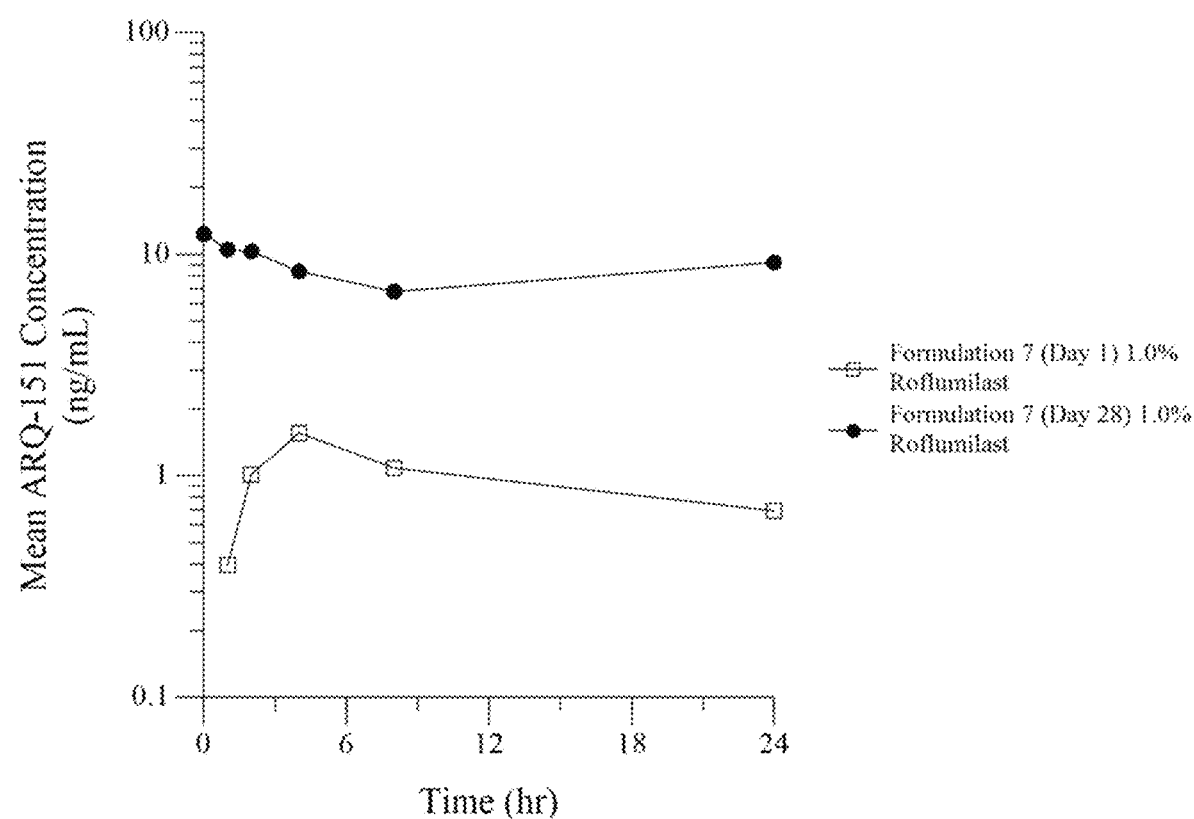
FIG. 6 is a line graph showing Day 1 and Day 28 PK profiles after once daily dosing of 1.0% roflumilast topical cream.

Two (2) grams of the cream Formulation 7 having varying concentrations of roflumilast, for each kg of pig weight was distributed over the clipped skin area by gentle inunction with a glass stirring rod or stainless-steel spatula. The cream was applied evenly with a thin, uniform film beginning at the scapular region and moving caudally over the test site. The width of the test site area was bilaterally divided by the spine. Twenty pigs (10 males and 10 females) were dosed with 1% roflumilast cream, twelve pigs (6 males and 6 females) were dosed with 0.5% roflumilast cream, and twelve pigs (6 males and 6 females) were dosed with 0.15% roflumilast cream, each dosed daily for 28 days. Six pigs (3 males and 3 females) were each dosed daily with 0.3% roflumilast cream (formulation 7) for 14-days. Blood was sampled from a suitable vein pre-dose (time=0), and at times 1, 2, 4, 8 and 24 hours post dose administration on day 1 and day 28 (or day 14 for 0.3% roflumilast) of dosing. The results are shown graphically in FIG. 3 (0.15% roflumilast cream), in FIG. 4 (0.3% roflumilast), in FIG. 5 (0.5% roflumilast cream), and in FIG. 6 (1.0% roflumilast cream) and in tabular form in Table 4.

As shown in each of FIGS. 3 to 6, the gradual ascent to Cmax is evident from the day 1 pharmacokinetic profile. What is most striking and surprising about the data shown in FIGS. 3 to 6 is the very flat and prolonged plateau in blood levels of the drug following Cmax in the day 28 or day 14 (0.3% roflumilast cream) pharmacokinetic profile, after reaching steady state drug delivery.

TABLE 4

| Topical Product Dosed | Trough (T = 0) (ng/ml) | Peak or Cmax (ng/ml) |
| --- | --- | --- |
| 0.15% Roflumilast Cream (FIG. 3—Steady State Day 28) | 4.5 (females) 5.0 (males) | 4.9 (females) 5.0 (males) |
| 0.3% Roflumilast Cream (FIG. 4—Steady State Day 14) | 3.7 (females) 6.6 (males) | 4.5 (females) 6.6 (males) |
| 0.5% Roflumilast Cream (FIG. 5—Steady State Day 28) | 8.5 (females) 6.7 (males) | 10.7 (females) 8.2 (males) |
| 1% Roflumilast Cream (FIG. 6—Steady State Day 28) | 16.3 (females) 8.4 (males) | 16.3 (females) 10.0 (males) |

Likewise, the data of Table 4 show an extremely small variation in blood concentration between the trough and peak (Cmax) following the attainment of steady state for each of the four concentrations of roflumilast when the formulation of the present invention is topically applied.

Example 6—Clinical Study in Subjects with Plaque Psoriasis

Study Design

ARQ-151 is a topical cream which contains roflumilast. This phase 1/2a clinical trial enrolled two cohorts: Cohort 1 evaluated a single administration of ARQ-151 cream 0.5% and Cohort 2 evaluated ARQ-151 cream 0.5% or 0.15% applied once daily for 28 days. In Cohort 1, subjects applied ARQ-151 cream 0.5% to 25 cm$^2$ of psoriatic plaque(s). Subjects were screened (Visit 1), returned to the clinic for treatment (Visit 2) and PK blood draws, had a follow-up visit at 24 hours after the baseline visit for a PK blood draw (Visit 3), and received a follow-up telephone contact for safety evaluation 7 days after Visit 3. Subjects enrolled in Cohort 1 could be enrolled in Cohort 2 if they met eligibility criteria; subjects from Cohort 1 who rolled into Cohort 2 had all of their plaque(s) treated in Cohort 2 up to 5% body surface area (BSA).

Cohort 2 used a parallel-group, double-blind, vehicle-controlled study design. Subjects were randomly assigned in a 1:1:1 ratio to ARQ-151 cream 0.5%, ARQ-151 cream 0.15%, or a matched vehicle, which was applied to all psoriatic plaques (except on the face, intertriginous areas, scalp, palms, and soles) up to an application area of 5% BSA. Subjects in Cohort 2 had screening and baseline visits, follow-up visits at weeks 1, 2, 3, and 4, an additional visit at day 29 for a final pharmacokinetic sample collection, and a follow-up telephone call for safety evaluation at week 5.

Cohort 1 received open-label treatment, without assignment or blinding. Assignment to treatment arm in Cohort 2 was performed using a computer-generated randomization list. Randomization was generated using SAS by an unblinded Premier Research statistician who was otherwise not involved in study conduct. The block size was 3; 72 total blocks were used. Everyone was blinded to treatment.

This study was conducted in accordance with the principles of the Declaration of Helsinki and Good Clinical Practice. The protocol was approved by Research Review Board, Inc., Richmond Hill, ON, Canada for all sites. All subjects provided written informed consent prior to initiation of any study-specific procedures. This trial was registered under ClinicalTrials.gov #NCT03392168.

Manufacture of ARQ-151 Cream (Formulation 7)

A target amount of 480 grams sterile water for irrigation-USP was accurately weighed into a 1000 ml glass beaker and 20 grams of sodium hydroxide pellets-NF was added and mixed using a stir bar until complete dissolution. This solution was set aside and labeled 1 N Sodium Hydroxide.

Target weights pf 1,000 grams white petrolatum-USP, 500 grams isopropyl palmitate-NF, and 1,000 grams of phosphate-ester self-emulsifying wax (CRODAFOS™ CES) were weighed into a 4 L glass beaker and heated on a hot plate to 75° C. to 80° C. while mixing with a propeller mixer. The mixture was labeled Oil Phase and was maintained at 75° C. to 80° C.

To the Main Manufacturing Vessel (a 20 L stainless steel vessel) a target weight of 4,225 grams of sterile water for irrigation-USP and a target weight 300 grams 1 N sodium hydroxide were added and heated on a hot plate to 75° C. to 80° C. This was recorded as the Aqueous Phase and was maintained at 75° C. to 80° C.

Target weights of 2,400 grams of Transcutol P-NF, 200 grams of hexylene glycol-NF, 20.0 grams of methylparaben-NF, and 5.0 grams of propylparaben NF were accurately weighed into a 7 L stainless steel beaker and propeller mixed until a clear homogeneous solution was obtained. Sufficient potency corrected roflumilast was added to this solution to obtain either a 0.15% roflumilast cream or a 0.5% roflumilast cream and this was labeled the API Phase.

The Oil Phase that was maintained at 75° C. to 80° C. was slowly added to the Aqueous Phase maintained at 75° C. to 80° C. in the Main Manufacturing Vessel with homogenizer mixing until a smooth, homogeneous cream was obtained. Using propeller mixing, the cream was cooled to 45° C. to 50° C. The API Phase was slowly added to the cream in the main manufacturing vessel and was mixed with the homogenizer. The pH of the finished cream was measured and adjusted to within the pH range of 5.1 to 5.9 using 1 N Sodium Hydroxide or Diluted Hydrochloric Acid, 10% (w/v)-NF. After bulk product release, the cream was filled into aluminum ¾"×3¾" #16 sealed white tubes and the tubes crimped to provide the primary container closure system.

Patients

To be eligible for enrollment in Cohort 1, subjects had to be ≥18 years of age with ≥25 cm$^2$ of chronic plaque psoriasis. To be eligible for enrollment in Cohort 2, subjects also had to have chronic plaque psoriasis of ≥6 months duration covering 0.5% to 5.0% of total BSA excluding the face, scalp, intertriginous areas, palms, and soles. Subjects needed to have at least 1 (and up to 3) target plaque(s)≥9 cm$^2$ in size with a Target Plaque Severity Score (TPSS)≥4. Target plaques could be located anywhere on the body (excluding the face, scalp, intertriginous areas, palms, and soles), including the knees and elbows. Key exclusion criteria included: non-plaque forms of psoriasis, drug-induced psoriasis, skin conditions that would interfere with study assessments, known allergies to excipients in ARQ-151 cream, hypersensitivity to PDE-4 inhibitors, inability to discontinue use of strong P-450 cytochrome inducers or P-450 cytochrome inhibitors, inability to refrain from use of a tanning bed, inability to discontinue systemic or topical therapies for the treatment of psoriasis, active infection requiring oral or intravenous antibiotics, antifungal, or antiviral agents within 7 days of baseline, or current or history of cancer within 5 years except for fully excised skin basal cell carcinoma, cutaneous squamous cell carcinoma, or cervical carcinoma.

Treatments and Application

Formulation 7, also known as ARQ-151 cream, contained 0.5% or 0.15% roflumilast. Vehicle contained all ingredients in the ARQ-151 cream except roflumilast. In Cohort 1, ARQ-151 cream 0.5% was applied in the clinic to 25 cm$^2$ of psoriatic plaque(s). In Cohort 2, all psoriatic lesions up to 5% BSA (except for those on the face, scalp, intertriginous areas, palms, and soles) were treated at home by subjects. Subjects were instructed by study staff on proper dosing and administration of ARQ-151 cream and vehicle.

Study Assessments

Assessments of efficacy (Cohort 2 only), pharmacokinetics (both cohorts), and safety (both cohorts) were conducted. The primary and secondary efficacy endpoints were calculated based on the product of Target Plaque Severity Score (TPSS) and Target Plaque Area (TPA). The TPSS was determined for each target plaque on each subject as the sum of erythema, thickness, and scaling scores, each rated on a scale of 0 (none) to 4 (very severe) and was identical to the severity scoring used in the PASI. TPA (cm$^2$) was determined by multiplying the longest diameter (cm) of the target plaque by the widest perpendicular diameter (cm). Thus, the product of TPSS×TPA was roughly analogous to a PASI for the treated plaque. TPSS and TPA assessments were conducted at screening, baseline, and weeks 1, 2, 3, and 4. Optional photography was performed at 4 centers at baseline and Visits 2, 3, 4, and 6.

Pharmacokinetic profiles for roflumilast and its active metabolite roflumilast N-oxide12 were determined from plasma. Blood samples for pharmacokinetic analyses were collected on day 1 at 1, 2, 4, and 6 hours after ARQ-151 application. On day 28, samples were collected before dosing (trough level) and at 1, 2, 4, 6, and 24 hours after application.

Safety endpoints included the type and incidence of treatment-emergent adverse events (TEAEs) and serious adverse events (SAEs); application site reactions; and changes in physical examinations, vital signs, electrocardiograms, and clinical laboratory parameters. Safety was assessed at all study visits and at telephone follow-up. Skin irritation was assessed on days 1 and 2 for Cohort 1 and at baseline and visits 3, 4, 5, and 6 for Cohort 2. Skin irritation was evaluated using a scale developed by Berger and Bowman13 ranging from 0 (no evidence of irritation) to 7 (strong reaction spreading beyond application site). Additionally, other clinical signs of irritation were scored on an 'A' (slight glazed appearance) to 'F' (small petechial erosions and/or scabs) scale. An additional safety endpoint was the results from the Depressive Symptomatology Questionnaire, 14 which was administered at screening, week 2, and week 4. The questionnaire is a 16-item inventory of depressive symptoms, with each item scored on a range of 0 to 3. Depression severity is based on score category, where total score 5 represents no depression; 6-10 represents mild depression; 11-15 represents moderate depression; 16-20 represents severe depression; and 21 represents very severe depression.

Statistical Considerations

For Cohort 2, a sample size of 24 subjects per arm (72 total subjects) was estimated to provide 80% power to detect a difference of 23% in the mean percentage change from baseline in the primary endpoint between the ARQ-151 cream and matching vehicle arm. This estimation was based on a 1-way analysis of variance at the $\alpha$=0.025 significance level. To accommodate a 16% drop-out rate, the total sample size was increased to 84 subjects.

TEAEs were coded using the Medical Dictionary for Regulatory Activities (MedDRA) version 20.1, and severity was graded on a 5-point scale of Grade 1 (mild), Grade 2 (moderate), Grade 3 (severe), Grade 4 (life-threatening consequences), or Grade 5 (death related to AE).

Pharmacokinetic parameters were calculated using the plasma concentration values of roflumilast and roflumilast N-oxide (ng/mL) at each nominal time point with Phoenix WinNonlin (v8.0) using standard noncompartmental analysis. The area under the concentration time curve (AUC) was estimated using the linear trapezoidal linear interpolation method. The maximum plasma concentration (Cmax) and time to reach maximum concentration (Tmax) were based on direct assessment. Sample concentration values reported to be below the limit of quantification (BLQ; <0.100 ng/mL) were ignored.

The primary efficacy endpoint was the difference in mean percentage change from baseline at week 4 in the product of TPSS×TPA between each dose of ARQ-151 cream and vehicle control. The primary efficacy endpoint was analyzed using a mixed model for repeated measures with center within country, treatment, study visit, and treatment-by-study-visit interaction as fixed effects and baseline TPSS× TPA score as a covariate. Mean differences between visit value and baseline were calculated for each treatment. Mean percentage change from baseline for each ARQ-151 dose and corresponding vehicle were compared using an unstructured covariance structure unless the model did not converge; in that case the appropriate covariance structure was investigated. The Bonferroni method was used to control for multiplicity, where the significance level for each of pairwise comparisons of active vs placebo was at $\alpha$=0.025.

Secondary efficacy endpoints included the difference in mean percentage change from baseline at weeks 1, 2, and 3 in composite TPSS×TPA score, TPSS, and TPA between each dose of ARQ-151 cream and vehicle control. Statistical analyses of secondary efficacy endpoints were the same as those used for the primary endpoint, except no adjustments for multiplicity were used and all analyses were conducted at the $\alpha$=0.05 level.

In a post hoc analysis, the percentage of subjects with 75% and 90% improvement from baseline in TPSS×TPA (75% responders and 90% responders) at each study visit through week 4 were also evaluated.

Safety analyses were conducted with the safety population, which comprised all subjects who received at least 1 dose of study drug and were based on treatment received. Pharmacokinetic analyses were conducted with the pharmacokinetic population, which included all subjects who consented for sampling and received active drug with sufficient plasma concentrations of roflumilast to define a profile. Efficacy analyses were conducted with the modified intent-to-treat population, which was composed of all subjects in Cohort 2 who received 1 dose of study drug and had 1 post-baseline efficacy evaluation.

No imputation was used for missing data. Data processing, tabulation of descriptive statistics, calculation of inferential statistics, and graphical representations (except for PK parameter estimation) were performed primarily using SAS (release 9.4). All PK parameter estimations were performed using WinNonlin® version 6.4 or later.

Results

Patients

Subjects were recruited from 7 study sites in Canada and from 1 site in the US between Dec. 5, 2017 (first patient enrolled) and May 2, 2018 (last follow-up visit). Eight subjects enrolled in Cohort 1, and 89 subjects enrolled in Cohort 2, including subjects randomly assigned to ARQ-151 cream 0.5% (N=30), ARQ-151 cream 0.15% (N=28), and vehicle (N=31). All subjects in Cohort 1 received treatment and completed the study, and 6 also participated in Cohort 2. Four subjects in Cohort 2 discontinued early from the study because of loss to follow-up (n=3) or other reasons (n=1). There were no discontinuations due to AEs. The safety populations comprised all 8 subjects in Cohort 1 and all 89 subjects in Cohort 2. The PK population included 20 subjects who received Formulation 7 (ARQ-151 cream) 0.5% and 22 subjects who received Formulation 7 (ARQ-151 cream) 0.15%. The efficacy population comprised all subjects in Cohort 2.

The mean age (standard deviation [SD]) was 51.6 (16.9) years for Cohort 1 and mean age ranged from 47.5 to 55.3 years across Cohort 2 treatment arms (Table 5). Most subjects were white. The average BSA of involvement was ~2% in all treatment groups. Of the 89 subjects enrolled in Cohort 2, 35 (39.3%) had target plaques located on the knees, elbows, or both.

TABLE 5

Subject Characteristics (Safety Population)

| | Cohort 1 | Cohort 2 | | |
| --- | --- | --- | --- | --- |
| | ARQ-151 0.5% (N = 8) | ARQ-151 0.5% (N = 30) | ARQ-151 0.15% (N = 28) | Vehicle (N = 31) |
| Age, mean years (SD) | 51.6 (16.9) | 49.9 (15.9) | 55.3 (13.2) | 47.5 (14.7) |
| Sex, n (%) | | | | |
| Male | 1 (12.5) | 16 (53.3) | 19 (67.9) | 18 (58.1) |
| Female | 7 (87.5) | 14 (46.7) | 9 (32.1) | 13 (41.9) |
| Race, n (%) | | | | |
| White | 8 (100) | 25 (83.3) | 24 (85.7) | 22 (71.0) |
| Asian | 0 | 2 (6.7) | 2 (7.1) | 8 (25.8) |
| Black/African American | 0 | 2 (6.7) | 2 (7.1) | 0 |
| Other | 0 | 1 (3.3) | 0 | 1 (3.2) |
| Psoriasis-affected BSA, mean m² (SD) | NC | 3.06 (1.39) | 2.73 (1.32) | 2.21 (1.05) |

BSA, body surface area;
NC, not collected;
SD, standard deviation.

Efficacy Results

Figure 7A:
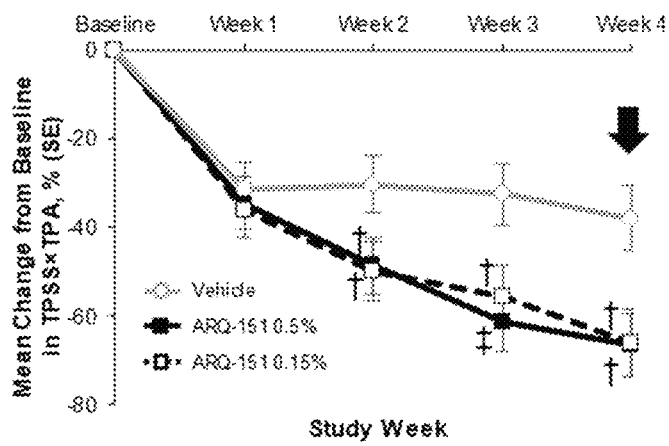
FIGS. 7A, 7B and 7C show changes in baseline in Target Plaque Severity Score and/or Target Plaque Area for 0.15% roflumilast topical cream and 0.5% roflumilast topical cream.

The primary efficacy endpoint was met: the mean percentage change from baseline in TPSS×TPA at week 4 was significantly different from vehicle for ARQ-151 cream 0.5% (P=0.0007) and ARQ-151 cream 0.15% (P=0.0011) (FIG. 7A). For both concentrations of ARQ-151 cream, 66%-67% improvement from baseline was observed in the primary endpoint after 4 weeks of treatment vs 38% for vehicle, based on least square (LS) mean percentage change from baseline. Statistical separation from vehicle was reached for both drug product concentrations as early as week 2 of treatment, and the difference between drug product and vehicle continued to increase through week 4. Both Formulation 7, ARQ-151 cream 0.5% and 0.15% showed similar efficacy in this primary endpoint throughout the study duration.

Figure 7B:
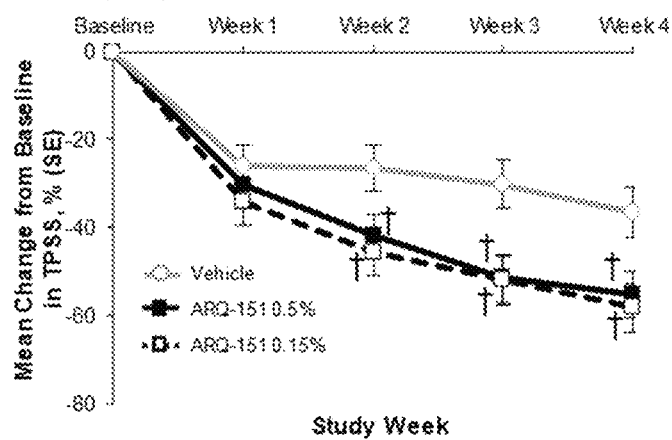
Figure 7C:
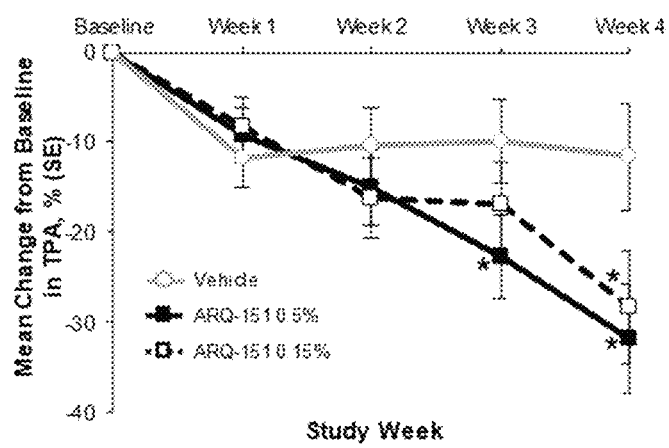

Secondary efficacy endpoints of change from baseline in TPSS (FIG. 7B) and change from baseline in TPA (FIG. 7C) were statistically significantly different between ARQ-151 at both active concentrations and vehicle after 4 weeks of treatment. For both active concentrations of ARQ-151 vs vehicle, change from baseline in TPSS, but not TPA, reached statistical significance as early as 2 weeks.

Patients receiving Formulation 7, ARQ-151 cream 0.5% and 0.15% and vehicle after 4 weeks of treatment were compared to baseline, along with their respective TPSS× TPA scores. Of note, the vehicle-treated subjects seemed to have improvement mainly in the appearance of scaling (predictable for an emollient cream). Both subjects receiving ARQ-151 cream 0.5% and 0.15% show examples of substantial improvement in the elbows or knees, which can be treatment-resistant areas of psoriasis. Indeed, 39.3% of subjects had target plaques on the elbows and/or knees.

In a post hoc analysis, 75% responder rates (75% improvement from baseline in TPSS×TPA) at week 4 were also evaluated. In the ARQ-151 cream 0.5% group, 10 subjects (35.7%) achieved this level of improvement (P=0.0090), and in the ARQ-151 cream 0.15% group, 7 subjects (25.9%) were 75% responders (P=0.0700). There were two 75% responders in the vehicle group. In this same analysis, 90% responder rates at week 4 were also evaluated. In the ARQ-151 cream 0.5% group, 4 subjects (14.3%) achieved this level of improvement, and in the ARQ-151 cream 0.15% group, 3 subjects (11.1%) were 90% responders; however, none of the 90% responder rates was statistically significant. There was one 90% responder in the vehicle group.

Pharmacokinetic Results

In Cohort 1, limited evidence of systemic plasma exposure to roflumilast or roflumilast N-oxide was observed after a single topical administration of ARQ-151 0.5% to 25 cm² of psoriatic plaques (data not shown). In Cohort 2, systemic plasma exposure to roflumilast and roflumilast N-oxide was observed following single or multiple applications of Formulation 7 (ARQ-151) to psoriatic plaques covering 0.5% to 5% BSA (Table 8, FIG. 8A for 0.5% Formulation 7, ARQ-151 cream and FIG. 8B for 0.15% Formulation 7, ARQ-151 cream). On day 1, roflumilast but not roflumilast N-oxide exposure appeared to increase in a dose-dependent manner. At day 28, the plasma concentration vs time profiles were relatively flat (very small peak to trough differences) suggesting that roflumilast and roflumilast N-oxide exposure achieved steady state and appeared to increase in a dose-dependent manner. The ratio of N-oxide to roflumilast after topical administration ranged from 4.7 to 5.9, compared with 12 after oral administration of roflumilast, the latter being higher due to increased contribution from first pass metabolism.

Figure 8A:
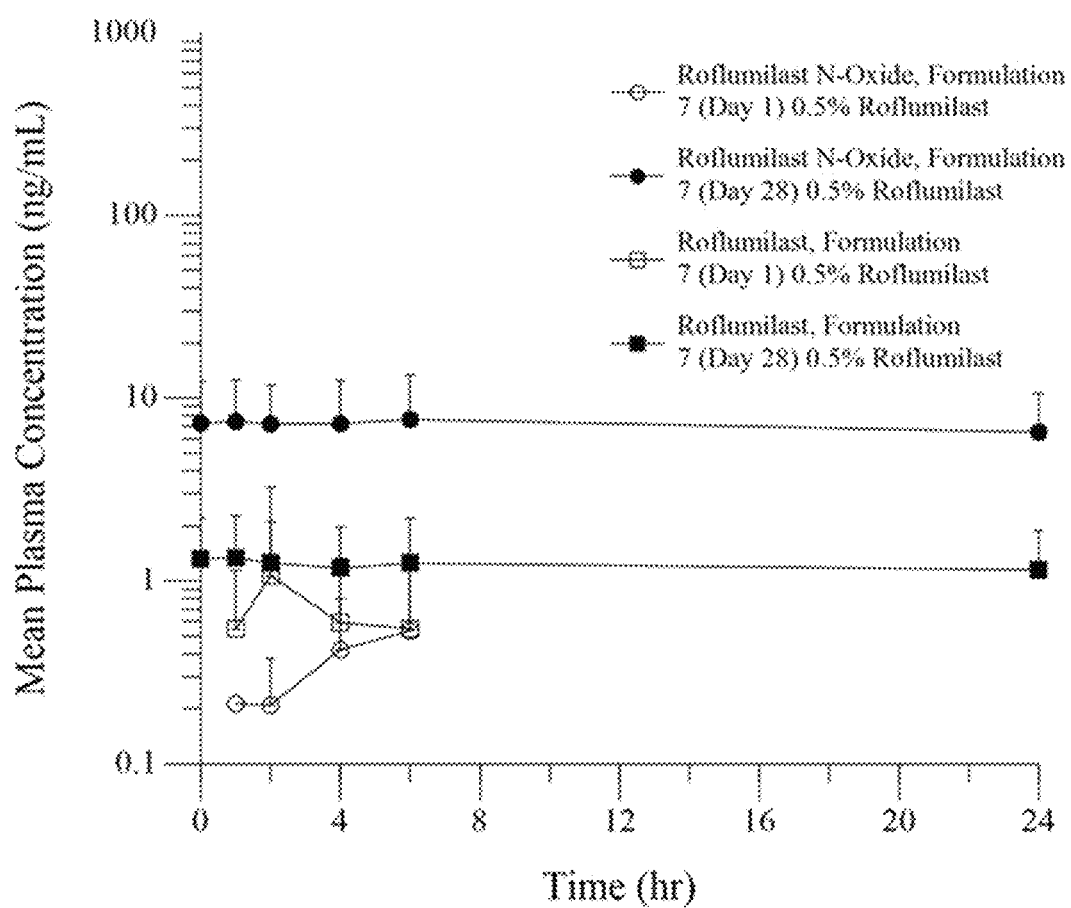
FIGS. 8A and 8B show roflumilast and roflumilast N-oxide plasma concentrations at day 1 and day 28 (pharmacokinetic population) for 0.15% roflumilast topical cream and 0.5% roflumilast topical cream.
Figure 8B:
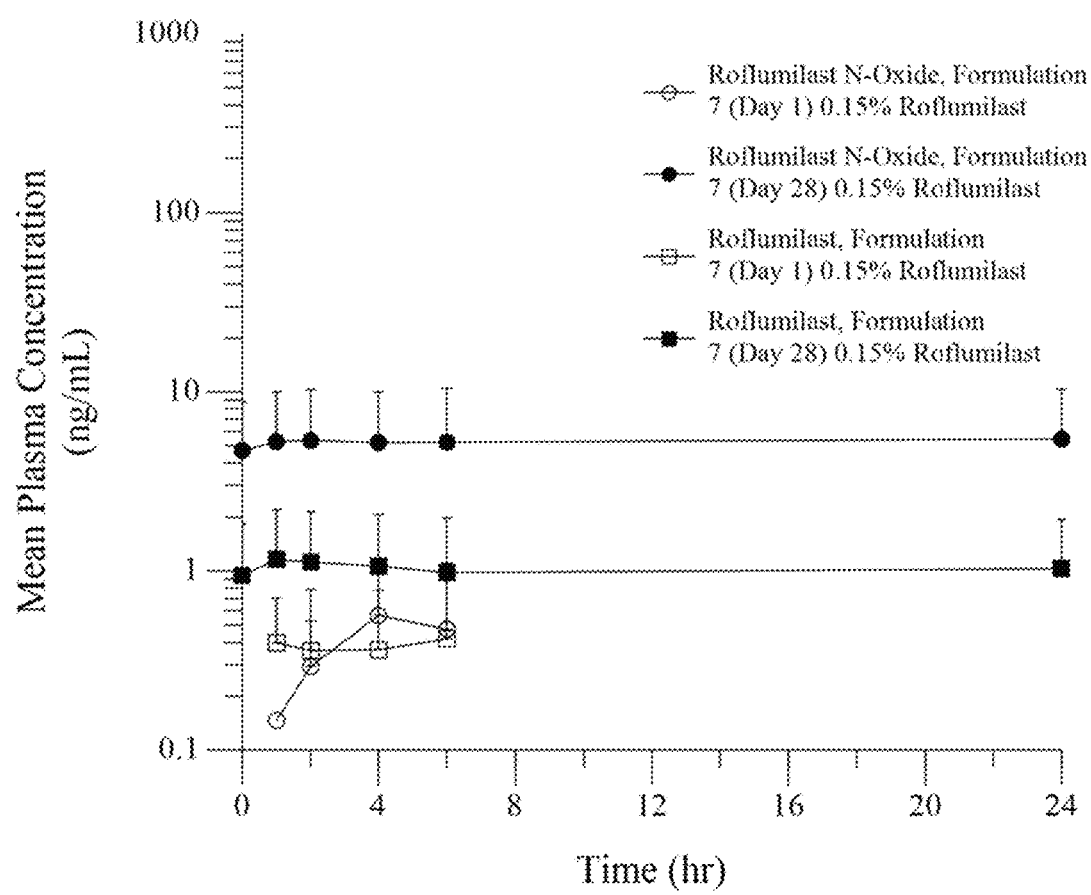

As shown in FIGS. 8A and 8B, when roflumilast is formulated in a cream containing the phosphate ester surfactant Crodafos CES, the gradual ascent to Cmax is evident in the single dose and steady-state pharmacokinetic profile. As shown in FIGS. 8A and 8B, there is a very flat and prolonged plateau in blood levels of the drug following Cmax for the 24-hours following the first application of 0.15% or 0.5% Formulation 7 (ARQ-151 cream) in human subjects. The pharmacokinetic profile of roflumilast after dosing the skin with Formulation 7 has the same low rise to Cmax shape when applied to humans or pigs.

TABLE 6

Pharmacokinetic Parameters (Pharmacokinetic Population; Cohort 2)

|  | ARQ-151 0.5% | ARQ-151 0.15% |
|---|---|---|
| Day 1 | | |
| Roflumilast | | |
| $AUC_{0-last}$, mean h × ng/ml (SD) [n] | 4.37 (5.84) [10] | 2.34 (2.56) [7] |
| $C_{max}$, mean ng/ml (SD) [n] | 1.38 (2.26) [10] | 0.578 (0.468) [7] |
| $T_{max}$, mean h {minimum, maximum} [n] | 3.20 {1.00, 6.00} [10] | 3.71 {1.00, 6.00} [7] |
| Roflumilast N-oxide | | |
| $AUC_{0-last}$, mean h × ng/ml (SD) [n] | 2.61 (2.13) [4] | 3.18 (2.54) [2] |
| $C_{max}$, mean ng/ml (SD) [n] | 0.965 (0.858) [4] | 1.07 (0.950) [2] |
| $T_{max}$, mean h [minimum, maximum] [n] | 6.00 {6.00, 6.00} [4] | 6.00 {6.00, 6.00} [2] |
| Day 28 | | |
| Roflumilast | | |
| $AUC_{0-last}$, mean h × ng/ml (SD) [n] | 29.2 (19.9) [20] | 24.4 (22.8) [21] |
| $C_{max}$, mean ng/ml (SD) [n] | 1.48 (0.978) [20] | 1.30 (1.06) [21] |
| $T_{max}$, mean h [minimum, maximum] [n] | 3.70 {0.00, 24.0} [20] | 4.95 {0.00, 24.0} [21] |
| Roflumilast N-oxide | | |
| $AUC_{0-last}$, mean h × ng/ml (SD) [n] | 172 (116) [20] | 127 (119) [22] |
| $C_{max}$, mean ng/ml (SD) [n] | 8.41 (5.54) [20] | 6.11 (5.53) [22] |
| $T_{max}$, mean h [minimum, maximum] [n] | 8.25 {0.00, 24.0} [20] | 8.59 {0.00, 24.0} [22] |

$AUC_{0-last}$, area under the concentration time curve until the last measurable time point;
$C_{max}$, maximum plasma concentration;
$T_{max}$, time to maximum plasma concentration.

Safety Results

In Cohort 1, only 1 subject reported a TEAE, which was considered unrelated to treatment (Table 9). In Cohort 2, the percent of TEAEs in the 0.15% group was lower than in the 0.5% or vehicle groups (7.1% vs 23.3% and 25.8%, respectively, for treatment-related TEAEs; and 25% vs 40% and 35.5%, respectively, for all TEAEs) (Table 9); all were mild or moderate in severity. No SAE was reported in this study, and no subject discontinued from the study because of a TEAE. All treatment-related TEAEs were associated with the application site, accounting for 17 events. Application site TEAEs were generally mild in severity and number (16 events were mild and 1 event was moderate) and showed no consistent differences between drug product and vehicle. No changes in physical examinations, vital signs, electrocardiograms, or clinical laboratory parameters were considered clinically meaningful. There were no clinically significant differences in weight changes between treatment groups. One subject in the 0.5% treatment group reported a single episode of nausea of moderate severity, but no further episodes in the remaining 3 weeks of the study. No subjects reported vomiting or diarrhea. No signs of skin irritation (dermal reactions) were noted in Cohort 1. For Cohort 2, mean (SD) dermal reaction scores at baseline for ARQ-151 cream 0.5%, 0.15%, and vehicle were 0.2 (0.5), 0.0 (0.2), and 0.2 (0.4), respectively, and at week 4 were 0.1 (0.5), 0.0 (0.0), and 0.1 (0.4).

TABLE 7

Summary of Safety (Safety Population)

| | Cohort 1 | Cohort 2 | | |
|---|---|---|---|---|
| | ARQ-151 0.5% (N = 8) | ARQ-151 0.5% (N = 30) | ARQ-151 0.15% (N = 28) | Vehicle (N =31) |
| Subjects with, n (%): | | | | |
| ≥1 TEAE | 1 (12.5) | 12 (40.0) | 7 (25.0) | 11 (35.5) |
| Treatment-related TEAE | 0 | 7 (23.3) | 2 (7.1) | 8 (25.8) |
| TEAE leading to discontinuation | 0 | 0 | 0 | 0 |
| SAE | 0 | 0 | 0 | 0 |
| Maximum severity of TEAEs, n (%) | | | | |
| Mild | 0 | 7 (23.3) | 3 (10.7) | 6 (19.4) |
| Moderate | 1 (12.5) | 5 (16.7) | 4 (14.3) | 5 (16.1) |
| Application site TEAEs, n (%) | | | | |
| Erythema | 0 | 4 (13.3) | 1 (3.6) | 4 (12.9) |
| Pain | 0 | 2 (6.7) | 1 (3.6) | 5 (16.1) |
| Edema | 0 | 1 (3.3) | 0 | 1 (3.2) |
| Papules | 0 | 1 (3.3) | 0 | 1 (3.2) |
| Pruritus | 0 | 1 (3.3) | 1 (3.6) | 0 |

SAE, serious adverse event;
TEAE, treatment-emergent adverse event.

DISCUSSION

In this phase 1/2a clinical trial, Formulation 7 (ARQ-151 cream) 0.5% and 0.15% was well tolerated, safe, and effective for the treatment of chronic plaque psoriasis. Formulation 7 (ARQ-151 cream) at both doses tested demonstrated strong efficacy as shown by statistically significant reductions in plaque severity and size compared to vehicle.

Statistically significant efficacy of ARQ-151 (Formulation 7 containing 0.15% or 0.5% roflumilast) as compared to vehicle in the primary study endpoint was observed with both active doses as early as 2 weeks after initiation of treatment, and differences between ARQ-151 and vehicle continued to increase through the last visit at 4 weeks. LS mean TPSS×TPA values decreased 38% with vehicle over the course of the study; the preponderance of this effect occurred during week 1 of treatment, which was likely contributed to by apparently decreased scaling to the observer's eye caused by the emollient cream. There was no difference in efficacy between ARQ-151 cream 0.5% and 0.15% in the primary endpoint (percentage change from baseline in TPSS×TPA) at week 4. However, the 75% responder rates at week 4 suggested the 0.5% cream was somewhat more efficacious (35.7%; P=0.0090 vs vehicle) than the 0.15% concentration (25.9%; P=0.0700). With both active drug concentrations after 4 weeks of dosing, TPSS×TPA values were already reduced by 66%-67% from baseline based on LS means. However, TPSS×TPA did not plateau in subjects treated with ARQ-151, suggesting that a longer duration of treatment might provide even greater efficacy.

The TPSS×TPA endpoint was chosen to be analogous to whole-body Psoriasis Area and Severity Index (PASI) measurements. Both use the same plaque severity scale, which was applied to 1-3 target lesions in the current study vs the entire body with PASI. The TPA 'area' function is different from the area of plaque involvement assessment in PASI, but we would propose that the product of TPSS×TPA provides an analogous assessment of 'target plaque(s)' to PASI for the entire body. Based on this assumption, the efficacy of topical ARQ-151 after 4 weeks of dosing (with 35.7% of subjects reaching 75% improvement for the 0.5% cream) may be comparable to that of the class 1 steroid betamethasone dipropionate 0.064% (32.7% PASI 75 response rate after 4 weeks of dosing) in the phase 3 studies of Taclonex®.

The safety profile of Formulation 7 (ARQ-151 cream) at both 0.5% and 0.15% was similar to vehicle, which is explained, at least in part, by the pharmacokinetic findings. When administered orally for COPD, roflumilast may be associated with gastrointestinal side effects (diarrhea, nausea), headache, and weight loss in a minority of patients. Typically, clinical development of PDE-4 inhibitors for oral use has been limited by gastrointestinal effects such as nausea and vomiting. Indeed, nausea, vomiting, and weight loss are believed to be mediated at the level of the brain. In contrast to oral administration, topical administration of roflumilast in our study was associated with a slow ascent to maximum plasma concentrations over multiple days, and a flat exposure to roflumilast and its active metabolite roflumilast N-oxide throughout the dosing period (i.e. $C_{max} \sim C_{min}$ across dosing interval). The lack of nausea and vomiting seen in the present study could possibly be attributed the lack of 'peak to trough' $C_{max}$ variation; lower $C_{max}$ values than observed following oral administration; or bypassing of the gastrointestinal tract with topical administration PDE-4 inhibition represents a validated mechanism of action for oral psoriasis therapy, but a new mechanism of action for topical psoriasis therapy. Patients with mild to moderate disease represent the majority of the psoriasis population. This patient population has not benefited from the recent introduction of biologic therapies, which are used in patients with more severe disease. However, it is not surprising that PDE-4 inhibition is an effective modality for the treatment of psoriasis. Apremilast was approved for the oral treatment of psoriasis in 2014. Crisaborole is currently approved at a 2% concentration for the treatment of atopic dermatitis. Roflumilast is a highly potent PDE-4 inhibitor, exhibiting half maximal inhibitory concentration ($IC_{50}$) values of both roflumilast and roflumilast N-oxide for the different PDE-4 isoforms and subtypes at subnanomolar potency. Rolumilast is 50- to 300-fold more potent than either apremilast or crisaborole against the different PDE-4 isoforms and subtypes. The oral dose of roflumilast, at only 0.5 mg per day, is reflective of this extremely high potency.

Example 7—Crisaborole Single and Multiple Dose Human Pharmacokinetics

As stated in the Eucrisa® package insert (Pfizer Labs, New York, NY) 2% crisaborole, a PDE4 inhibitor, is formulated as a topical ointment composed of white petrolatum, propylene glycol, mono- and diglycerides, paraffin, butylated hydroxytoluene and edetate calcium disodium. This formulation does not contain a phosphate ester surfactant.

Figure 9:
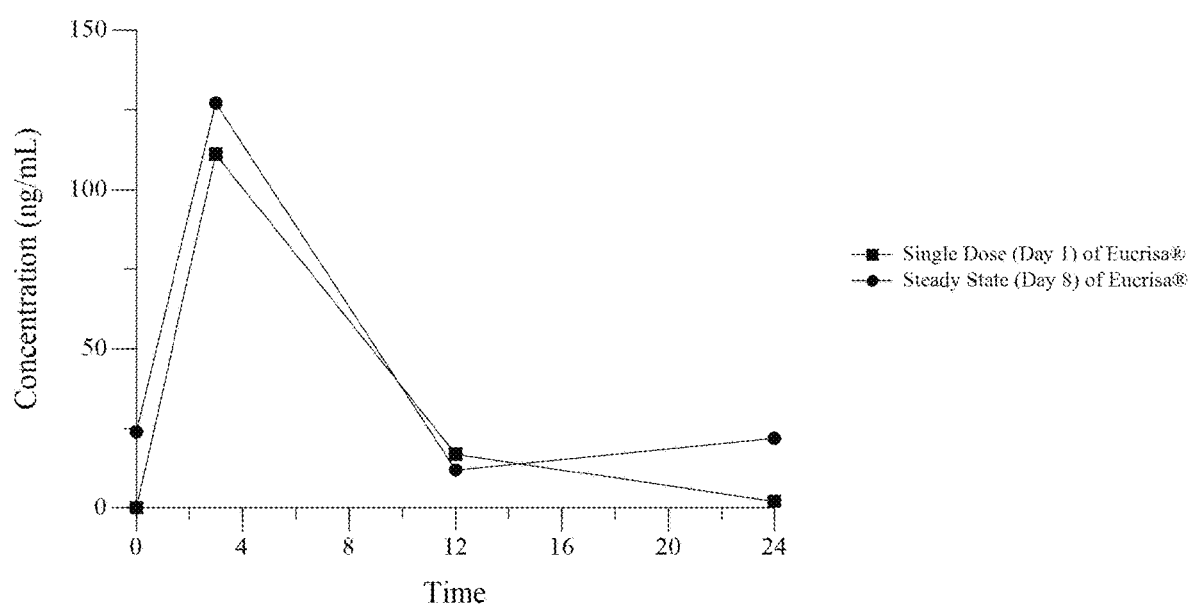
FIG. 9 is a line graph showing Day 1 single dose and Day 8 steady state pharmacokinetic profiles for the PDE4 inhibitor crisaborole after application of once daily Eucrisa® topical ointment.

Atopic dermatitis patients having 25% or greater body surface area of diseased skin applied Eucrisa® ointment once daily. Single dose (day 1) pharmacokinetics for crisaborole, the PDE4 inhibitor active in Eucrisa®, were published in the non-confidential portion of the Summary Basis of Approval (SBOA) and are reproduced in FIG. 9. For the same patients, steady-state pharmacokinetic data for crisaborole were obtained on day 8 after once daily treatment with Eucrisa®. This steady state pharmacokinetic data was obtained from the Eucrisa® SBOA and is reproduced in FIG. 9. As seen, the PDE4 inhibitor crisaborole, when dosed from a commercialized topical ointment, rapidly rises to a Cmax spike at 4 hours and then drops to near pre-dose levels within 24-hours of once daily dosing. This high Cmax spike of the PDE4 inhibitor occurs after a single topical application and after steady-state dosing of once daily ointment applications.

Example 8—Single Dose Pharmacokinetics of Crisaborole Delivered from a Crodafos CES Cream Compared to Delivery of Roflumilast from the Same Cream Crisaborole (0.3% w/w) was formulated as cream Formulation 8 by combining Crodafos CES (a commercial blend of cetostearyl alcohol, dicetyl phosphate and ceteth-10 phosphate), diethylene glycol monoethyl ether, as well as other ingredients to create a complete marketable formulation. Formulation 8 has the same excipients in the same ratios as Formulation 7 of this invention. The only difference between the two formulations is that Formulation 8 contains 0.3% crisaborole as the PDE-4 inhibitor drug active and Formulation 7 contains 0.3% roflumilast as the PDE-4 inhibitor drug active. Both formulations were buffered with NaOH to obtain a pH of 5.5.

TABLE 8

| Ingredient | Formulation 7 | Formulation 8 |
| --- | --- | --- |
| PDE4 Inhibitor | 0.3% Roflumilast | 0.3% w/w Crisaborole |
| Petrolatum, USP | 10.0% w/w | 10.0% w/w |
| Isopropyl Palmitate, NF | 5.0% w/w | 5.0% w/w |
| Crodafos CES | 10.0% w/w | 10.0% w/w |
| cetostearyl alcohol | (6-8% w/w) | (6-8% w/w) |
| dicetyl phosphate | (1-2% w/w) | (1-2% w/w) |
| ceteth-10 phosphate | (1-2% w/w) | (1-2% w/w) |

TABLE 8-continued

| Ingredient | Formulation 7 | Formulation 8 |
| --- | --- | --- |
| Diethylene Glycol Monoethyl Ether, NF | 25.0% w/w | 25.0% w/w |
| Hexylene Glycol, NF | 2.0% w/w | 2.0% w/w |
| Methylparaben, NF | 0.20% w/w | 0.20% w/w |
| Propylparaben, NF | 0.050% w/w | 0.050% w/w |
| 1N NaOH, NF | q.s. ad pH 5.5 | q.s. ad pH 5.5 |
| Purified Water, USP | q.s. ad 100% | q.s. ad 100% |

Male and female swine (Gottingen Minipig®) were ordered to weigh 8 to 12 kg at arrival. On the day prior to administration of a topical cream containing roflumilast, the hair was clipped from the back of each animal. The pigs were sedated for the shaving procedure. Care was taken to avoid abrading the skin.

Two (2) grams of the cream Formulation 8 (containing 0.3% crisaborole) for each kg of pig weight was distributed over the clipped skin area by gentle inunction with a glass stirring rod or stainless-steel spatula. The cream was applied evenly with a thin, uniform film beginning at the scapular region and moving caudally over the test site. The width of the test site area was bilaterally divided by the spine. Twelve pigs (6 males and 6 females) were dosed once with 0.3% crisaborole cream (formulation 8). Six pigs (3 males and 3 females) were dosed once with 0.3% roflumilast (formulation 7). Blood was sampled from a suitable vein pre-dose (time=0), and at times 1, 2, 4, 8 and 24-hours post dose administration. The single dose results for these two PDE-4 inhibitors are shown graphically in FIG. 10

Figure 10:
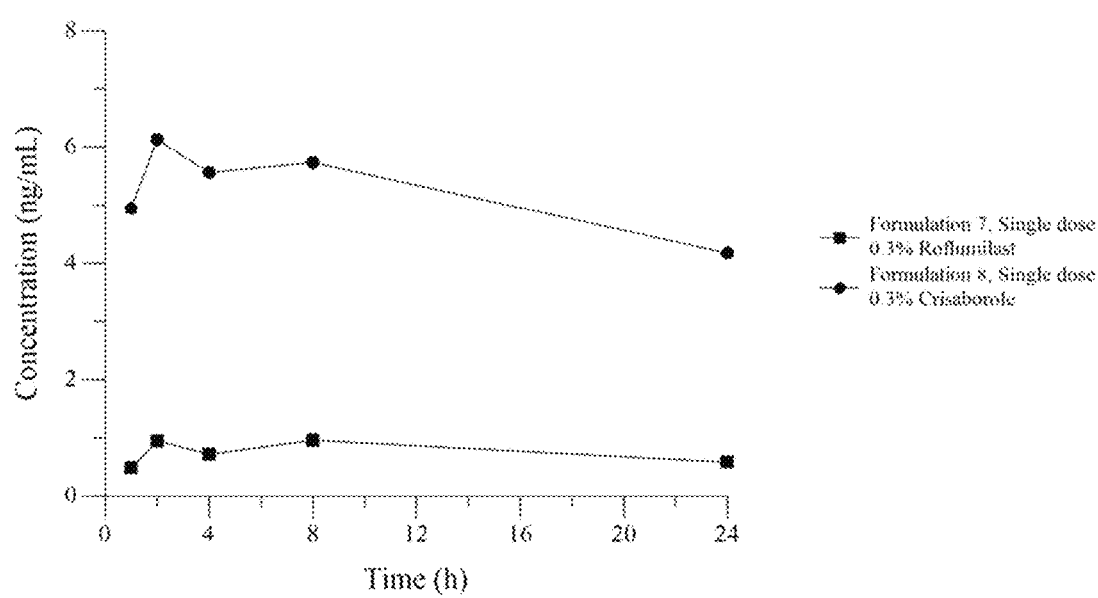
FIG. 10 is a line graph showing Day 1 single dose PK profiles after once daily dosing of Crodafos-CES creams containing either 0.3% crisaborole or 0.3% roflumilast.

As shown in FIG. 10, when a PDE-4 inhibitor is formulated in a cream containing the phosphate ester surfactant Crodafos CES, the gradual ascent to Cmax is evident in the single dose pharmacokinetic profile. What is most striking and surprising about the data shown in FIG. 10 is the very flat and prolonged plateau in blood levels of the drug following Cmax for the 24-hours following the first application of 0.3% crisaborole cream in the pig. The pharmacokinetic profile of the PDE4 inhibitors roflumilast and crisaborole have the same low rise to Cmax shape when delivered from the same Crodafos CES cream formulation. This low rise to Cmax PK profile is not seen with topical formulations of roflumilast or crisaborole when topically applied in formulations the do not contain Crodafos CES.

Further modifications, uses, and applications of the invention described herein will be apparent to those skilled in the art. It is intended that such modifications be encompassed in the following claims.

The invention claimed is:

1. A pharmaceutical composition for topical administration comprising:
   (i) roflumilast, wherein the roflumilast is in an amount of 0.05-1% w/w;
   (ii) a phosphate ester surfactant blend comprising cetostearyl alcohol, dicetyl phosphate and ceteth-10 phosphate, wherein the phosphate ester surfactant blend is in an amount of 1.0-25% w/w; and
   (iii) water;
   wherein said pharmaceutical composition is in the form of a foam, and
   wherein the $C_{max}$ of roflumilast from the topical composition is reduced relative to an oral roflumilast formulation marketed under the trademark DALIRESP®.

2. The composition of claim 1, wherein said composition further comprises a propellant.

3. The composition of claim 2, wherein said propellant is a blend of propane, isobutane, and n-butane.

4. The composition of claim 2, wherein said phosphate ester surfactant blend is in an amount of 2% w/w.

5. The composition of claim 2, wherein said composition further comprises diethylene glycol monoethyl ether.

6. The composition of claim 5, wherein said diethylene glycol monoethyl ether is in an amount of 10-40% w/w.

7. The composition of claim 2, wherein said roflumilast is in an amount of 0.3% w/w.

8. The composition of claim 2, wherein said roflumilast is in an amount of 0.15% w/w.

9. The composition of claim 2, wherein said roflumilast is in an amount of 0.05% w/w.

10. The composition of claim 2, wherein said phosphate ester surfactant blend is in an amount sufficient to decrease a slope of the plasma concentration curve of the roflumilast between administration of said composition and Cmax.

11. The composition of claim 2, wherein the plasma concentration curve of the roflumilast has no spike at $C_{max}$.

12. A pharmaceutical composition for topical administration comprising:
   (i) roflumilast, wherein the roflumilast is in an amount of 0.05-1% w/w;
   (ii) a phosphate ester surfactant blend comprising cetostearyl alcohol, dicetyl phosphate and ceteth-10 phosphate, wherein the phosphate ester surfactant blend is in an amount of 1.0-25% w/w;
   wherein said pharmaceutical composition is in the form of a foam, and
   wherein the peak to trough ratio of roflumilast blood plasma concentration is less than 2 at steady state.

13. The composition of claim 12, wherein said composition further comprises a propellant.

14. The composition of claim 13, wherein said propellant is a blend of propane, isobutane, and n-butane.

15. The composition of claim 13, wherein said phosphate ester surfactant blend is in an amount of 2% w/w.

16. The composition of claim 13, wherein said composition further comprises diethylene glycol monoethyl ether.

17. The composition of claim 16, wherein said diethylene glycol monoethyl ether is in an amount of 10-40% w/w.

18. The composition of claim 13, wherein said roflumilast is in an amount of 0.3% w/w.

19. The composition of claim 13, wherein said roflumilast is in an amount of 0.15% w/w.

20. The composition of claim 13, wherein said roflumilast is in an amount of 0.05% w/w.

21. The composition of claim 13, wherein the difference in a trough and an adjacent peak of the plasma concentration curve of the roflumilast at steady state is between about 4% and about 7%.

22. The composition of claim 13, wherein the plasma concentration of the roflumilast plateaus after $C_{max}$ for 24 hours following administration.

23. The composition of claim 13, wherein the peak to trough ratio is approximately 1 at steady state.

* * * * *